US012746295B2

(12) United States Patent
Wang et al.

(10) Patent No.: US 12,746,295 B2
(45) Date of Patent: Sep. 29, 2026

(54) DCAS13-MEDIATED THERAPEUTIC RNA BASE EDITING FOR IN VIVO GENE THERAPY

(71) Applicant: University of Massachusetts, Boston, MA (US)

(72) Inventors: Dan Wang, Worcester, MA (US); Guangping Gao, Worcester, MA (US); Jiaming Wang, Worcester, MA (US)

(73) Assignee: University of Massachusetts, Westborough, MA (US)

( * ) Notice: Subject to any disclaimer, the term of this patent is extended or adjusted under 35 U.S.C. 154(b) by 832 days.

(21) Appl. No.: 17/918,714

(22) PCT Filed: Apr. 13, 2021

(86) PCT No.: PCT/US2021/027103
§ 371 (c)(1),
(2) Date: Oct. 13, 2022

(87) PCT Pub. No.: WO2021/211598
PCT Pub. Date: Oct. 21, 2021

(65) Prior Publication Data
US 2023/0346978 A1 Nov. 2, 2023

Related U.S. Application Data

(60) Provisional application No. 63/009,984, filed on Apr. 14, 2020.

(51) Int. Cl.

| | |
|---|---|
| ***A61K 48/00*** | (2006.01) |
| ***A61P 43/00*** | (2006.01) |
| ***C12N 9/22*** | (2006.01) |
| ***C12N 9/78*** | (2006.01) |
| ***C12N 15/11*** | (2006.01) |
| ***C12N 15/86*** | (2006.01) |

(52) U.S. Cl.
CPC .......... *A61K 48/0066* (2013.01); *A61P 43/00* (2018.01); *C12N 9/22* (2013.01); *C12N 9/78* (2013.01); *C12N 15/11* (2013.01); *C12N 15/86* (2013.01); *C12Y 305/04004* (2013.01); *C12N 2310/20* (2017.05); *C12N 2750/14143* (2013.01)

(58) Field of Classification Search
None
See application file for complete search history.

(56) References Cited

U.S. PATENT DOCUMENTS

| | | | | |
|---|---|---|---|---|
| 2003/0073232 | A1 | 4/2003 | Wilson et al. | |
| 2014/0147432 | A1 | 5/2014 | Bancel et al. | |
| 2014/0171485 | A1 | 6/2014 | Bancel et al. | |
| 2017/0283887 | A1 | 10/2017 | Wielscher et al. | |
| 2019/0241633 | A1 | 8/2019 | Fotin-Mleczek et al. | |
| 2021/0403925 | A1* | 12/2021 | Chevessier-Tünnesen | C12N 15/113 |
| 2022/0033785 | A1* | 2/2022 | Liu | C12N 15/62 |
| 2022/0184229 | A1* | 6/2022 | Gersbach | C12N 15/113 |

FOREIGN PATENT DOCUMENTS

| | | | | |
|---|---|---|---|---|
| WO | WO 2011/045765 A1 | 4/2011 | | |
| WO | WO 2018/191388 A1 | 10/2018 | | |
| WO | WO 2019/005884 A1 | 1/2019 | | |
| WO | WO 2019/169004 A1 | 9/2019 | | |
| WO | WO202/014261 A1 * | 1/2020 | | A61K 38/00 |
| WO | WO 2020/028555 A2 | 2/2020 | | |

OTHER PUBLICATIONS

Cox, et al. RNA editing with CRISPR-Cas13. Science. Nov. 24, 2017; 358(6366):1019-1027 (Year: 2017).*
Zhou et al. Deletion of the B-B' and C-C' regions of inverted terminal repeats reduces rAAV productivity but increases transgene expressionScientific Reports vol. 7, Article No. 5432 (2017) (Year: 2017).*
Extended European Search Report for Application No. 21788684.5, mailed May 27, 2024.
International Search Report and Written Opinion for Application No. PCT/US2021/027103, mailed Jun. 8, 2021.
International Preliminary Report on Patentability for Application No. PCT/US2021/027103, mailed Oct. 27, 2022.

* cited by examiner

*Primary Examiner* — Tiffany Nicole Grooms
(74) *Attorney, Agent, or Firm* — Wolf, Greenfield & Sacks, P.C.

(57) ABSTRACT

Aspects of the disclosure relate to compositions (e.g., isolated nucleic acids, rAAV vectors, rAAVs, etc.) and methods for gene editing. The disclosure is based, in part, on isolated nucleic acids encoding combinations of gene editing proteins (e.g., Cas proteins) and base editors (e.g., Adenosine Deaminase Acting on RNA deaminase domains) with certain regulatory sequences that are amenable to packaging in recombinant adeno-associated viruses (rAAVs). In some embodiments, compositions described by the disclosure are useful for treating certain diseases in a subject in need thereof.

11 Claims, 5 Drawing Sheets

Specification includes a Sequence Listing.

| | Previous version editor | AAV compatible editor |
|---|---|---|
| Promoter | CMV | u1a |
| dCas13b | Full length or Truncation form | Truncation form |
| Orientation of editor | N-dCas13b-ADARDD-C | N-dCas13b-ADARDD-C<br>N-ADARDD-dCas13b-C |
| Localization signal | NES | NLS or NES |
| Tag for detection | NO | HA |

DCAS13-MEDIATED THERAPEUTIC RNA BASE EDITING FOR IN VIVO GENE THERAPY

RELATED APPLICATIONS

This application is a national stage filing under 35 U.S.C. § 371 of international PCT application PCT/US2021/027103, filed Apr. 13, 2021, which claims priority under 35 U.S.C. § 119 (e) to U.S. provisional patent application, U.S. Ser. No. 63/009,984, filed Apr. 14, 2020, the entire contents of each of which are incorporated herein by reference.

REFERENCE TO AN ELECTRONIC SEQUENCE LISTING

The contents of the electronic sequence listing (U012070139US01-SUBSEQ-LJG.txt; Size: 46,412 bytes; and Date of Creation: May 6, 2026) are herein incorporated by reference in their entirety.

BACKGROUND dCas13-Adenosin Deaminase base editors have been used to corrected mutations on the mRNA level. However, due to the large size of the base size of the current base editors, they are not amenable to Adeno-associated virus (AAV) mediated gene delivery. In vivo editing efficiency and therapeutic efficacy of dCas13-Adenosin Deaminase base editors remain challenging.

SUMMARY

Aspects of the disclosure relate to compositions (e.g., isolated nucleic acids, rAAV vectors, rAAVs, etc.) and methods for gene editing. The disclosure is based, in part, on isolated nucleic acids encoding combinations of gene editing proteins (e.g., Cas proteins) and base editors (e.g., Adenosine Deaminase Acting on RNA deaminase domains) with certain regulatory sequences that are amenable to packaging in recombinant adeno-associated viruses (rAAVs). In some embodiments, isolated nucleic acids and vectors described herein do not exceed the packaging capacity of recombinant adeno-associated virus (rAAV) particles.

In some aspects, the disclosure provides an isolated nucleic acid comprising an expression cassette encoding a first region comprising a catalytically inactive Cas13b (e.g., dCas13b) protein; a second region comprising a first signal sequence; a third region comprising an Adenosine Deaminase Acting on RNA deaminase domain (ADARdd); and a fourth region comprising a second signal sequence, wherein the expression cassette is flanked by adeno-associated virus (AAV) inverted terminal repeats (ITRs), and the size of the construct is less than 5 kb. In some embodiments, the size of the construct is less than 4.7 kb.

In some embodiments, an AAV ITR is an AAV2 ITR. In some embodiments, at least one ITR is a truncated ITR, for example a mTR or AITR. In some embodiments, an isolated nucleic acid encodes a self-complementary AAV (scAAV) vector.

Aspects of the disclosure relate to isolated nucleic acids encoding a RNA-guided nuclease (RGN). In some embodiments, the RGN is a Cas protein, or a Cas protein variant, for example a catalytically inactive Cas protein, also referred to as a "dead Cas" or "dCas" protein. In some embodiments, the RGN is a dCas13b protein. In some embodiments, a Cas protein (or dCas protein) is truncated relative to the wild-type Cas protein from which it is derived. In some embodiments, a dCas13b protein comprises (or consists of) the amino acid sequence set forth in SEQ ID NO: 1 or is encoded by the nucleic acid sequence set forth in SEQ ID NO: 10

Aspects of the disclosure relate to isolated nucleic acids encoding a base editing protein (also referred to as a base editor). In some embodiments, a base editor introduces an A to G mutation or an A to C mutation on a target sequence (e.g., a sequence to which the base editor is directed, for example by a gRNA-Cas protein complex). In some embodiments, a base editor introduces a C to T mutation on a target sequence. In some embodiments, a base editor is an Adenosine Deaminase Acting on RNA deaminase domain (ADARdd). In some embodiments, an ADARdd protein comprises one or more amino acid substitutions, insertions, or deletions (e.g., truncations) relative to the wild-type ADARdd from which it is derived. In some embodiments, an ADARdd comprises (or consists of) the amino acid sequence set forth in SEQ ID NO: 2 or is encoded by the nucleic acid sequence set forth in SEQ ID NO: 9

The disclosure is based, in part, on the recognition that the presence of a nuclear export signal (NES) or a nuclear localization signal (NES) sequence affects the efficiency of base editing in the context of rAAV-mediated delivery. In some embodiments, rAAVs comprising NLS sequences mediate enhanced (e.g., increased) base editing relative to rAAVs comprising NES sequences. In some embodiments, a first signal sequence is a nuclear export signal (NES) or a nuclear localization signal (NLS). In some embodiments, a second signal sequence is a nuclear export signal (NES) or a nuclear localization signal (NLS). In some embodiments, an NES comprises (or consists of) the nucleic acid sequence set forth in SEQ ID NO: 3. In some embodiments, an NLS comprises (or consists of) the nucleic acid sequence set forth in SEQ ID NO: 4.

In some embodiments, an isolated nucleic acid further comprises one or more (e.g., 1, 2, 3, 4, 5, or more) linking polynucleotides. In some embodiments, a linking polynucleotide encodes a glycine-serine (GS) linker.

In some embodiments, an isolated nucleic acid further comprises a promoter. Aspects of the disclosure relate to the recognition that inclusion of certain primers in isolated nucleic acids and rAAV vectors result in improved base editing in vivo relative to rAAVs comprising other promoters (e.g., CMV promoters). In some embodiments, an isolated nucleic acid described herein does not comprise (e.g., lacks) a cytomegalovirus (CMV) promoter. In some embodiments, an isolated nucleic acid does not comprise a CMV enhancer sequence.

The disclosure is based, in part, on isolated nucleic acids comprising promoters that are smaller in size than conventionally used promoters, which facilitates packaging of the isolated nucleic acids into rAAV particles. In some embodiments, a promoter is a Ula promoter, H1 promoter, or a small synthetic promoter. Examples of small synthetic promoters are known, for example Jet promoter, and are described by Redden et al. *Nature Communications* volume 6, Article number: 7810 (2015).

The architecture (e.g., structural orientation) of the isolated nucleic acids can vary. In some embodiments, a promoter is operably linked to the second region. In some embodiments, a promoter is operably linked to the third region. In some embodiments, a first region is upstream of (e.g., 5' relative to) a third region. In some embodiments, a second region is upstream of (e.g., 5' relative to) a first region. In some embodiments, a third region is upstream of (e.g., 5' relative to) a first region. In some embodiments, a second region is downstream of (e.g., 3' relative to) a third region. In some embodiments, an isolated nucleic acid further comprises a poly-adenylation (polyA) signal. In some embodiments, a polyA signal is a rabbit beta-globulin polyA (RGB polyA).

In some aspects, the disclosure provides an isolated nucleic acid comprising the sequence set forth in any one of SEQ ID NOs: 5-10.

In some aspects, the disclosure provides a recombinant adeno-associated virus (rAAV) comprising an isolated nucleic acid as described herein; and an AAV capsid protein. In some embodiments, a capsid protein is an AAV1, AAV2, AAV3, AAV4, AAV5, AAV6, AAV7, AAV8, AAV9 capsid protein, or a variant thereof.

In some aspects, the disclosure provides a pharmaceutical composition comprising an isolated nucleic acid or rAAV as described herein, and a pharmaceutically acceptable excipient.

In some aspects, the disclosure provides a method for base editing in a cell, the method comprising introducing an isolated nucleic acid or the rAAV as described herein, into a cell. In some embodiments, the cell is a mammalian cell, for example a human cell. In some embodiments, the cell is in a subject (e.g., the cell is in vivo).

In some embodiments, the method further comprises introducing one or more guide RNAs (gRNAs) into the cell. In some embodiments, the one or more gRNAs target a gene of interest, for example a gene of interest comprising one or more G to A nucleic acid substitutions. In some embodiments, a cell comprises one or more G to A substitutions.

In some aspects, the disclosure provides a method for treating a disease characterized by one or more G to A substitutions in a gene of interest in a subject, the method comprising administering to the subject an isolated nucleic acid or the rAAV as described herein. In some embodiments, a subject is a human.

In some embodiments, the method further comprises administering one or more gRNAs that specifically bind (e.g., hybridize) to a region of the gene of interest containing the G to A substitutions.

In some embodiments, the one or more G to A substitutions results in the gene of interest having one or more premature termination codons (PTCs). In some embodiments, the gene of interest is Idua. In some embodiments, the disease is Hurler syndrome.

BRIEF DESCRIPTION OF DRAWINGS

FIG. 1A shows schematic designs of the structure of previously described dCas13-ADARdd editor and gRNA.

FIG. 1B shows a table and schematic designs of dCas13-ADARdd editors that are amenable to rAAV packaging. dCas13 protein can be placed at either the N terminal or C terminal of ADARdd. A NLS signal or NES signal can be placed either at the C terminal or N terminal of the protein coding sequences. An HA tag can be added between protein coding sequences for detection. Each of the vectors shown include a short Ula promoter, catalytic dead and truncation version Cas13 protein, ADARdd with E488Q/T375G double mutations, GS linkers, and RGB polyA sequence. FIG. 1C shows schematic design for vectors encoding gRNAs. The vector is in a self-complementary AAV (scAAV) vector. Human U6 promoter and terminator are used to express gRNA. EGFP coding sequence is used as a stuffer.

FIG. 2A shows the Cluc W85X reporter sequence with G→A pre-mature stop mutation in W85 codon. gRNA structure and sequence with example spacer length and mismatch distance is also shown. C-A mismatch was introduced in the gRNA sequence to enhance the ADAR editing. FIG. 2B shows the Cluc activity restoration with four different editors and tiled gRNAs. The data points are shown in mean value with SEM, three biological repeats of each point are included.

FIG. 3A shows nucleic acid and amino acid sequences of Idua-wt and Idua-W392X mutation. The W392X site is highlighted. The bystander Adenosines are labeled with numbers related to G→A mutation site (A0). − means upstream, + means downstream. FIG. 3B shows the liver mRNA A→G restoration editing in Idua-W392X mice by the editors. Bystander off-targets are also shown in the heat map. FIG. 3C shows IDUA enzymatic activity restoration in the Idua-W392X mice liver. The dashed line represents the therapeutic threshold, i.e., 0.5% of WT level. Error bars represent SD. Statistical analysis was performed with one-way ANOVA followed by Tukey's multiple comparisons test.

FIG. 4A shows the vector genome copies (GC) of editor and gRNA transgenes in the liver of Idua-W392X mice injected with rAAV. FIG. 4B shows the normalized editor transcript copies in the liver of Idua-W392X mice injected with rAAV. FIG. 4C shows IDUA enzymatic activity restoration in treated Idua-W392X mice liver is correlated with NES editor and gRNA gene delivery efficiency. FIG. 4D shows IDUA activity restoration in treated Idua-W392X mice liver is correlated with NLS editor and gRNA gene delivery efficiency. Error bars represent SD. Statistical analysis was performed with one-way ANOVA followed by Tukey's multiple comparisons test. The correlation analysis was performed with XY computer correlation followed by Pearson R analysis.

DETAILED DESCRIPTION

Figure 1A:
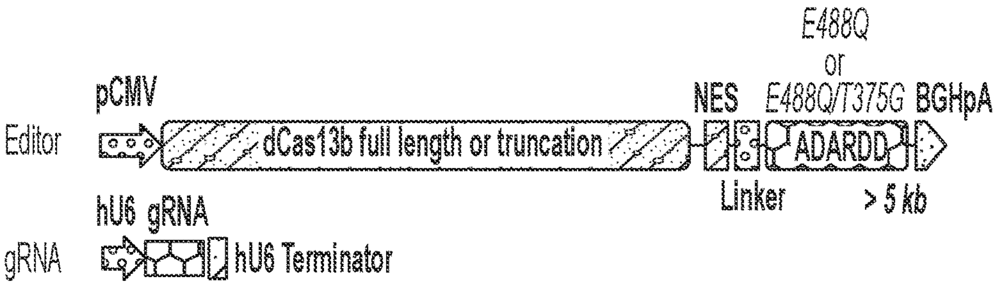
FIGS. 1A-1C show examples of dCas13-ADARDD editors and gRNAs.

Aspects of the disclosure relate to compositions (e.g., isolated nucleic acids, rAAV vectors, rAAVs, etc.) and methods for gene editing. The disclosure is based, in part, on isolated nucleic acids encoding combinations of gene editing proteins (e.g., Cas proteins) and base editors (e.g., Adenosine Deaminase Acting on RNA deaminase domains) with certain regulatory sequences that are amenable to packaging in recombinant adeno-associated viruses (rAAVs). In some embodiments, isolated nucleic acids and vectors described herein do not exceed the packaging capacity of recombinant adeno-associated virus (rAAV) particles.

In some aspects, the disclosure provides an isolated nucleic acid comprising an expression cassette encoding a first region comprising a catalytically inactive Cas13b (e.g., dCas13b) protein; a second region comprising a first signal sequence; a third region comprising an Adenosine Deaminase Acting on RNA deaminase domain (ADARdd); and a fourth region comprising a second signal sequence, wherein the expression cassette is flanked by adeno-associated virus (AAV) inverted terminal repeats (ITRs), and the size of the construct is less than 5 kb. In some embodiments, the size of the construct is less than 4.7 kb.

Isolated Nucleic Acids

A "nucleic acid" sequence refers to a DNA or RNA sequence. In some embodiments, proteins and nucleic acids of the disclosure are isolated. As used herein, the term "isolated" means artificially produced. As used herein, with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

In some embodiments, an isolated nucleic acid comprises an expression cassette encoding a first region comprising a RNA-guided nuclease (RGN). Examples of RGNs include but are not limited to Cas13 nucleases, Cas9 nucleases, Cas6 nucleases, Cfp1 nucleases, and variants thereof. A variant of a RGN may comprise or consist of a nucleic acid sequence that comprises one or more substitutions, insertions, and/or deletions relative to a wild-type RGN nucleic acid sequence. In some embodiments, an RGN is a catalytically inactive RGN, such as an RGN that retains RNA binding functionality but lacks nuclease activity. In some embodiments, a catalytically inactive RGN is a dead Cas13 nuclease. In some embodiments, a dead Cas13 nuclease is a dead Cas13b nuclease (e.g., a Cas13b nuclease that lacks nuclease activity but retains RNA binding activity). Cas13b derived from various organisms have been described, see, e.g., Cox et al., RNA Editing with CRISPR-Cas13, Science. 2017 Nov. 24; 358 (6366): 1019-1027. Non-limiting examples of Cas13b are set forth in Table 1 below.

TABLE 1

| Exemplary Cas13b | | | |
|---|---|---|---|
| Cas13b ID | Cas13b Abbreviation | Host Organism | Protein Accession |
| Cas13b1 | BzoCas13b | *Bergeyella zoohelcum* | WP_002664492 |
| Cas13b2 | PinCas13b | *Prevotella intermedia* | WP_036860899 |
| Cas13b3 | PbuCas13b | *Prevotella buccae* | WP_004343973 |
| Cas13b4 | AspCas13b | *Alistipes* sp. ZOR0009 | WP_047447901 |
| Cas13b5 | PsmCas13b | *Prevotella* sp. MA2016 | WP_036929175 |

TABLE 1-continued

| Exemplary Cas13b | | | |
|---|---|---|---|
| Cas13b ID | Cas13b Abbreviation | Host Organism | Protein Accession |
| Cas13b6 | RanCas13b | *Riemerella anatipestifer* | WP_004919755 |
| Cas13b7 | PauCas13b | *Prevotella aurantiaca* | WP_025000926 |
| Cas13b8 | PsaCas13b | *Prevotella saccharolytica* | WP_051522484 |
| Cas13b9 | Pin2Cas13b | *Prevotella intermedia* | WP_061868553 |
| Cas13b10 | CcaCas13b | *Capnocytophaga canimorsus* | WP_013997271 |
| Cas13b11 | PguCas13b | *Porphyromonas gulae* | WP_039434803 |
| Cas13b12 | PspCas13b | *Prevotella* sp. P5-125 | WP_044065294 |
| Cas13b13 | FbrCas13b | *Flavobacterium branchiophilum* | WP_014084666 |
| Cas13b14 | PgiCas13b | *Porphyromonas gingivalis* | WP_053444417 |
| Cas13b15 | Pin3Cas13b | *Prevotella intermedia* | WP_050955369 |

In some embodiments, the dCas13b is a PspCas13b. In some embodiments, the PspCas13b is a truncated form as compared to the wild-type PspCas13b. In some embodiments, the PspCas13b comprises an amino acid sequence at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 1. In some embodiments, the isolated nucleic acid comprises an expression cassette encoding a PspCas13b comprising an amino acid sequence at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 1. In some embodiments, a PspCas13b is encoded by a nucleic acid at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 10.

In some embodiments, the expression cassette of the isolated nucleic acid further encodes a third region comprising an Adenosine Deaminase Acting on RNA deaminase domain (ADARdd). Adenosine deaminases acting on RNA (ADAR) are enzymes responsible for binding to RNA and converting adenosine (A) to inosine (I) by deamination (e.g., Samuel et al., (2012). Adenosine deaminases acting on RNA (ADARs) and A-to-I editing. Heidelberg: Springer. ISBN 978-3-642-22800-1). ADAR protein is a RNA-binding protein, which functions in RNA-editing through post-transcriptional modification of mRNA transcripts by changing the nucleotide content of the RNA. The conversion from A to I in the RNA disrupt the normal A:U pairing which makes the RNA unstable. Inosine is structurally similar to guanine (G) which leads to I to cytosine (C) binding. Inosine typically mimics guanosine during translation. Codon changes can arise from editing which may lead to changes in the coding sequences for proteins and their functions (see, e.g., Lich et al., Inosine induces context-dependent recoding and translational stalling, Nucleic Acids Res. 2019 Jan. 10; 47 (1): 3-14; Nishikura, Functions and Regulation of RNA Editing by ADAR Deaminases, Annu Rev Biochem. 2010; 79:321-349). In some embodiments, the expression cassette encodes the deaminase domain (ADARdd) of an ADAR (e.g., ADAR lacking the RNA binding domain) or a variant thereof. In some embodiments, the ADARdd is an ADAR2dd. In some embodiments, an ADARdd variant has improved A-I editing efficiency (e.g., Fry et al., RNA Editing as a Therapeutic Approach for Retinal ene Therapy Requiring Long Coding Sequences, Int. J. Mol. Sci. 2020, 21, 777). In some embodiments, an ADAR2dd protein comprises one or more amino acid substitutions, insertions, or deletions (e.g., truncations) relative to the wild-type ADAR2dd from which it is derived. In some embodiments, the ADAR2dd variant comprises a mutation at amino acid residue E488 as compared to a wild-type ADAR2dd. In some embodiments, the mutation is E488Q as compared to a wild-type ADAR2dd. In some embodiments, the ADAR2dd variant comprises a mutation at amino acid residue T375 as compared to a wild-type ADAR2dd. In some embodiments, the mutation is T375G as compared to a wild-type ADAR2dd. In some embodiments, the ADAR2dd variant comprises a mutation at amino acid residue E488 and a mutation at amino acid residue T375 as compared to a wild-type ADAR2dd. In some embodiments, the mutations are E488Q/T375G as compared to a wild-type ADAR2dd. In some embodiments, the expression cassette encodes an ADAR2dd having E488Q/T375G mutations. In some embodiments, an ADAR2dd comprising E488Q/T375G mutations comprises an amino acid sequence at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 2. In some embodiments, the isolated nucleic acid comprises an expression cassette encoding an ADAR2dd E488Q/T375G comprising an amino acid sequence at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 2. In some embodiments, an ADAR2dd E488Q/T375G is encoded by a nucleic acid at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 9. In some embodiments, the ADARdd is capable of a C-to-U conversion. ADAR having C-to-U conversion has been previously described, e.g., in Abudayyeh et al., A cytosine deaminase for programmable single-base RNA editing, Science 26 *July* 2019: Vol. 365, Issue 6451, pp. 382-386).

In some embodiments, the expression cassette further encodes a second region comprising a first signal sequence. In some embodiments, the expression cassette further encodes a fourth region comprising a second signal sequence. In some embodiments, the first signal sequence is a nuclear export signal (NES). In some embodiments, the first signal sequence is a nuclear localization signal (NLS). In some embodiments, the second signal sequence is a nuclear export signal (NES). In some embodiments, the second signal sequence is a nuclear localization signal (NLS). In some embodiments, the first signal sequence is a NES, and the second signal sequence is a NES. In some embodiments, the first signal sequence is a NLS, and the second signal sequence is a NLS. In some embodiments, the first signal sequence is a NES, and the second signal sequence is a NLS. In some embodiments, the first signal sequence is a NLS, and the second signal sequence is a NES. Any NES known in the art can be used in the isolated nucleic acid described herein, e.g., NES described in NESbase—a database of nuclear export signals (cbs.dtu.dk/databases/NESbase/). Any NLS known in the art can be used in the isolated nucleic acid described herein, e.g., NLS described in NLSdb—Database of nuclear localization signals (rostlab.org/services/nlsdb/. In some embodiments, the NES is encoded by a nucleic acid sequence at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 3. In some embodiments, the NLS is encoded a nucleic acid sequence at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to in SEQ ID NO: 4. A nuclear localization signal (NLS) is an amino acid sequence that 'tags' a protein for import into the cell nucleus by nuclear transport. A nuclear export signal (NES) is a short target peptide containing 4 hydrophobic residues in a protein that targets it for export from the cell nucleus to the cytoplasm through the nuclear pore complex using nuclear transport. In some embodiments, the expression encodes a NLS and/or NES to facilitate the nuclear localization and/or export of the first region (e.g., adCas13b) and/or the second region (e.g., an ADARdd).

In some embodiments, each region of the expression cassette can be directly fused to each other, or fused by a polypeptide linker. Polypeptide linker have been previously described, e.g., in Chen et al., Fusion Protein Linkers: Property, Design and Functionality, *Adv Drug Deliv Rev.* 2013 Oct. 15; 65 (10): 1357-1369. In some embodiments, linkers with shorter length is ore compatible with the isolated nucleic acid described herein because of the packaging size limitation of an AAV vector. In some embodiments, the polypeptide linker is a glycine-serine (GS) linker. In some embodiments, the expression cassette comprises one or more GS linker between the regions fused by linkers.

In some embodiment, each of the regions of the expression cassette can be placed upstream (e.g., 5' relative to) or downstream (e.g., 3' relative to) of each other. In some embodiments, the first region (e.g., the dCas13b) is upstream of the third region (e.g., the ADARdd). In some embodiments, the first region (e.g., the dCas13b) is downstream of the third region (e.g., the ADARdd). In some embodiments, the second region is a NLS, and is placed upstream of the first region (e.g., dCas13b). In some embodiments, the second region is a NES, and is placed upstream of the first region (e.g., dCas13b). In some embodiments, the second region is a NLS, and is placed downstream of the first region (e.g., dCas13b). In some embodiments, the second region is a NES, and is placed downstream of the first region (e.g., dCas13b). In some embodiments, the fourth region is a NLS, and is placed upstream of the third region (e.g., ADARdd). In some embodiments, the fourth region is a NES, and is placed upstream of the third region (e.g., ADARdd). In some embodiments, the fourth region is a NLS, and is placed downstream of the third region (e.g., ADARdd). In some embodiments, the fourth region is a NES, and is placed downstream of the third region (e.g., ADARdd). In some embodiments, the expression cassette, from 5' to 3', comprises a NLS, a dCas13b, a GS linker, a NLS, a GS linker, and an ADARdd. In some embodiments, the expression cassette, from 5' to 3', comprises a NES, a dCas13b, a GS linker, a NES, a GS linker, and an ADARdd. In some embodiments, the expression cassette, from 5' to 3', comprises an ADARdd, a GS linker, a NLS, a GS linker, a dCas13b, a GS linker, and a NLS. In some embodiments, the expression cassette, from 5' to 3', comprises an ADARdd, a GS linker, a NES, a GS linker, a dCas13b, a GS linker, and a NES.

In some embodiments, the expression cassette of the isolated nucleic acid further comprises a promoter operably linked to the first region. In some embodiments, the expression cassette of the isolated nucleic acid further comprises a promoter operably linked to the third region. In some embodiments, the expression cassette of the isolated nucleic acid further comprises a promoter operably linked to the first region and the third region. In some embodiments, the expression cassette of the isolated nucleic acid further comprises a promoter operably linked to the first region, second region, and the third region. In some embodiments, the expression cassette of the isolated nucleic acid further comprises a promoter operably linked to the first region, second region, the third region and fourth region. In some embodiments, the expression cassette comprises one or more nucleic acid sequences operably linked to one or more promoters. The promoters may be the same promoters or different promoters. In some embodiments, two nucleic acid sequences are operably linked to the same promoter. In some embodiments, the promoter is a chicken beta-actin (CB) promoter or a murine small nuclear RNA (U1a) promoter. a human U6 promoter, a H1 promoter, or a small synthetic promoter.

As used herein, a nucleic acid sequence (e.g., coding sequence) and regulatory sequences are said to be "operably linked" when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame.

A "promoter" refers to a DNA sequence recognized by the synthetic machinery of the cell, or introduced synthetic machinery, required to initiate the specific transcription of a gene. The phrases "operatively linked," "operatively positioned," "under control" or "under transcriptional control" means that the promoter is in the correct location and orientation in relation to the nucleic acid to control RNA polymerase initiation and expression of the gene. In some embodiments, a transgene comprises a nucleic acid sequence encoding a RGN (e.g., a Cas13b nuclease) operably linked to a first promoter and a multi-gRNA expression cassette operably linked to a second promoter.

Generally, a promoter can be a constitutive promoter, inducible promoter, or a tissue-specific promoter.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is an RNA pol II promoter. In some embodiments, a promoter is an RNA pol III promoter, such as U6 or H1. In some embodiments, a promoter is an RNA pol II promoter. In some embodiments, a nucleic acid encoding a RGN is operably linked to a CB6 promoter. In some embodiments, a nucleic acid sequence encoding a multi-RNA expression cassette is operably linked to a RNA pol III promoter. In some embodiments, the RNA pol III promoter is a U6 promoter. In some embodiments, the promoter is a Ula promoter.

Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: retinoschisin proximal promoter, interphotoreceptor retinoid-binding protein enhancer (RS/IRBPa), rhodopsin kinase (RK), liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (α-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some aspects, the disclosure relates to isolated nucleic acids comprising an expression cassette that comprises one or more miRNA binding sites. Without wishing to be bound by any particular theory, incorporation of miRNA binding sites into gene expression constructs allows for regulation of transgene expression (e.g., inhibition of transgene expression) in cells and tissues where the corresponding miRNA is expressed. In some embodiments, incorporation of one or more miRNA binding sites into a transgene allows for de-targeting of transgene expression in a cell-type specific manner. In some embodiments, one or more miRNA binding sites are positioned in a 3' untranslated region (3' UTR) of a transgene, for example between the last codon of a nucleic acid sequence encoding a Cas13b protein or the ADARdd protein, and a poly A sequence.

In some embodiments, a transgene comprises one or more (e.g., 1, 2, 3, 4, 5, or more) miRNA binding sites that de-target expression of the dCas13b-ADARdd protein from central nervous system (CNS) cells. In some embodiments, a transgene comprises one or more (e.g., 1, 2, 3, 4, 5, or more) miRNA binding sites that de-target expression of the RGN or the multi-gRNA expression cassette from immune cells. In some embodiments, an expression cassette comprises one or more (e.g., 1, 2, 3, 4, 5, or more) miRNA binding sites that de-target expression of the dCas13b-ADARdd from immune cells (e.g., antigen presenting cells (APCs), such as macrophages, dendrites, etc.). Incorporation of miRNA binding sites for immune-associated miRNAs may de-target transgene expression from antigen presenting cells and thus reduce or eliminate immune responses (cellular and/or humoral) produced in the subject against products of the transgene, for example as described in US 2018/0066279, the entire contents of which are incorporated herein by reference.

As used herein an "immune-associated miRNA" is an miRNA preferentially expressed in a cell of the immune system, such as an antigen presenting cell (APC). In some embodiments, an immune-associated miRNA is an miRNA expressed in immune cells that exhibits at least a 2-fold, 3-fold, 4-fold, 5-fold, 6-fold, 7-fold, 8-fold, 9-fold, 10-fold higher level of expression in an immune cell compared with a non-immune cell (e.g., a control cell, such as a HeLa cell, HEK293 cell, mesenchymal cell, etc.). In some embodiments, the cell of the immune system (immune cell) in which the immune-associated miRNA is expressed is a B cell, T cell, Killer T cell, Helper T cell, γδ T cell, dendritic cell, macrophage, monocyte, vascular endothelial cell, or other immune cell. In some embodiments, the cell of the immune system is a B cell expressing one or more of the following markers: B220, BLAST-2 (EBVCS), Bu-1, CD19, CD20 (L26), CD22, CD24, CD27, CD57, CD72, CD79a, CD79b, CD86, chB6, D8/17, FMC7, L26, M17, MUM-1, Pax-5 (BSAP), and PC47H. In some embodiments, the cell of the immune system is a T cell expressing one or more of the following markers: ART2, CD1a, CD1d, CD11b (Mac-1), CD134 (OX40), CD150, CD2, CD25 (interleukin 2 receptor alpha), CD3, CD38, CD4, CD45RO, CD5, CD7, CD72, CD8, CRTAM, FOXP3, FT2, GPCA, HLA-DR, HML-1, HT23A, Leu-22, Ly-2, Ly-m22, MICG, MRC OX 8, MRC OX-22, OX40, PD-1 (Programmed death-1), RT6, TCR (T cell receptor), Thy-1 (CD90), and TSA-2 (Thymic shared Ag-2). In some embodiments, the immune-associated miRNA is selected from: miR-15a, miR-16-1, miR-17, miR-18a, miR-19a, miR-19b-1, miR-20a, miR-21, miR-29a/b/c, miR-30b, miR-31, miR-34a, miR-92a-1, miR-106a, miR-125a/b, miR-142-3p, miR-146a, miR-150, miR-155, miR-181a, miR-223 and miR-424, miR-221, miR-222, let-7i, miR-148, and miR-152.

In some embodiments, an expression cassette comprises various regions as described herein is a multicistronic cassette. In some embodiments, a multicistronic expression construct comprises two or more expression cassettes encoding one or more region (e.g., the first region and the third region) described herein.

In some embodiments, multicistronic expression constructs are comprise expression cassettes that are positioned in different ways. For example, in some embodiments, a multicistronic expression construct is provided in which a first expression cassette (e.g., an expression cassette encoding dCas13b, or portion thereof) is positioned adjacent to a second expression cassette (e.g., an expression cassette encoding an ADARdd, or a portion thereof). In some embodiments, a multicistronic expression construct is provided in which a first expression cassette comprises an intron, and a second expression cassette is positioned within the intron of the first expression cassette. In some embodiments, the second expression cassette, positioned within an intron of the first expression cassette, comprises a promoter and a nucleic acid sequence encoding a gene product operatively linked to the promoter.

In different embodiments, multicistronic expression constructs are provided in which the expression cassettes are oriented in different ways. For example, in some embodiments, a multicistronic expression construct is provided in which a first expression cassette is in the same orientation as a second expression cassette. In some embodiments, a multicistronic expression construct is provided comprising a first and a second expression cassette in opposite orientations.

The term "orientation" as used herein in connection with expression cassettes, refers to the directional characteristic of a given cassette or structure. In some embodiments, an expression cassette harbors a promoter 5' of the encoding nucleic acid sequence, and transcription of the encoding nucleic acid sequence runs from the 5' terminus to the 3' terminus of the sense strand, making it a directional cassette (e.g. 5'-promoter/(intron)/encoding sequence-3'). Since virtually all expression cassettes are directional in this sense, those of skill in the art can easily determine the orientation of a given expression cassette in relation to a second nucleic acid structure, for example, a second expression cassette, a viral genome, or, if the cassette is comprised in an AAV construct, in relation to an AAV ITR.

For example, if a given nucleic acid construct comprises two expression cassettes in the configuration 5'-promoter 1/encoding sequence 1 - - - promoter2/encoding sequence 2-3', the expression cassettes are in the same orientation, the arrows indicate the direction of transcription of each of the cassettes. For another example, if a given nucleic acid construct comprises a sense strand comprising two expression cassettes in the configuration 5'-promoter 1/encoding sequence 1 - - - encoding sequence 2/promoter 2-3', the expression cassettes are in opposite orientation to each other and, as indicated by the arrows, the direction of transcription of the expression cassettes, are opposed. In this example, the strand shown comprises the antisense strand of promoter 2 and encoding sequence 2.

For another example, if an expression cassette is comprised in an AAV construct, the cassette can either be in the same orientation as an AAV ITR, or in opposite orientation. AAV ITRs are directional. For example, the 3'ITR would be in the same orientation as the promoter1/encoding sequence 1 expression cassette of the examples above, but in opposite orientation to the 5'ITR, if both ITRs and the expression cassette would be on the same nucleic acid strand.

A large body of evidence suggests that multicistronic expression constructs often do not achieve optimal expression levels as compared to expression systems containing only one cistron. One of the suggested causes of sub-par expression levels achieved with multicistronic expression constructs comprising two or more promoter elements is the phenomenon of promoter interference (see, e.g., Curtin J A, Dane A P, Swanson A, Alexander I E, Ginn S L. Bidirectional promoter interference between two widely used internal heterologous promoters in a late-generation lentiviral construct. Gene Ther. 2008 March; 15 (5): 384-90; and Martin-Duque P, Jezzard S, Kaftansis L, Vassaux G. Direct comparison of the insulating properties of two genetic elements in an adenoviral vector containing two different expression cassettes. Hum Gene Ther. 2004 October; 15 (10): 995-1002; both references incorporated herein by reference for disclosure of promoter interference phenomenon). Various strategies have been suggested to overcome the problem of promoter interference, for example, by producing multicistronic expression constructs comprising only one promoter driving transcription of multiple encoding nucleic acid sequences separated by internal ribosomal entry sites, or by separating cistrons comprising their own promoter with transcriptional insulator elements. All suggested strategies to overcome promoter interference are burdened with their own set of problems, though. For example, single-promoter driven expression of multiple cistrons usually results in uneven expression levels of the cistrons. Further some promoters cannot efficiently be isolated and isolation elements are not compatible with some gene transfer vectors, for example, some retroviral vectors.

In some embodiments, a multicistronic expression construct is provided that allows efficient expression of a first encoding nucleic acid sequence driven by a first promoter and of a second encoding nucleic acid sequence driven by a second promoter without the use of transcriptional insulator elements. Various configurations of such multicistronic expression constructs are provided herein, for example, expression constructs harboring a first expression cassette comprising an intron and a second expression cassette positioned within the intron, in either the same or opposite orientation as the first cassette. Other configurations are described in more detail elsewhere herein.

In some embodiments, multicistronic expression constructs are provided allowing for efficient expression of two or more encoding nucleic acid sequences. In some embodiments, the multicistronic expression construct comprises two expression cassettes. In some embodiments, a first expression cassette of a multicistronic expression construct as provided herein comprises a first RNA polymerase II promoter and a second expression cassette comprises a second RNA polymerase II promoter. In some embodiments, a first expression cassette of a multicistronic expression construct as provided herein comprises an RNA polymerase II promoter and a second expression cassette comprises an RNA polymerase III promoter.

The isolated nucleic acids of the disclosure may be recombinant adeno-associated virus (AAV) vectors (rAAV vectors). In some embodiments, an isolated nucleic acid as described by the disclosure comprises adeno-associated virus (AAV) inverted terminal repeats (ITRs), or a variant thereof. The isolated nucleic acid (e.g., the recombinant AAV vector) may be packaged into a capsid protein and administered to a subject and/or delivered to a selected target cell.

"Recombinant AAV (rAAV) vectors" are typically composed of, at a minimum, an expression cassette and its regulatory sequences, and 5' and 3' AAV inverted terminal repeats (ITRs). The isolated nucleic acid may comprise a region encoding, for example, a protein and/or an expression control sequence (e.g., a poly-A tail), as described elsewhere in the disclosure.

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid further comprises a region (e.g., a second region, a third region, a fourth region, etc.) comprising a second AAV ITR. In some embodiments, an isolated nucleic acid encoding a transgene is flanked by AAV ITRs (e.g., in the orientation 5'-ITR-transgene-ITR-3'). In some embodiments, the AAV ITRs are AAV2 ITRs. In some embodiments, at least one of the AAV ITRs is a AITR, which lacks a terminal resolution site and induces formation of a self-complementary AAV (scAAV) vector. In some embodiments, the AAV ITRs are selected from the group consisting of AAV1 ITR, AAV2 ITR, AAV3 ITR, AAV4 ITR, AAV5 ITR, and AAV6 ITR.

An expression cassette of an isolated nucleic acid described by the disclosure may further comprises a polyadenylation (poly A) sequence. In some embodiments, a transgene comprises a poly A sequence is a rabbit beta-globulin (RBG) poly A sequence. In some embodiments, a transgene comprises a poly A sequence is a rabbit beta-globulin (RBG) poly A sequence, In some embodiments, the isolated nucleic acid comprises a nucleic acid sequence at least a70%, at least 75%, at least 80%, at least 85%, at least 90%, at least 91%, at least 92%, at least 93%, at least 94%, at least 95%, at least 96%, at least 97%, at least 98%, at least 99%, or 100% identical to any one of SEQ ID NOs: 5-10.

In some aspects, the present disclosure also provides a separate isolated nucleic acid encoding one or more guide RNAs to be delivered with (e.g., concurrently or sequentially) with the isolated nucleic acid comprising an expression cassette encoding a first region comprising a catalytically inactive Cas13b (e.g., dCas13b) protein; a second region comprising a first signal sequence; a third region comprising an Adenosine Deaminase Acting on RNA deaminase domain (ADARdd); and a fourth region comprising a second signal sequence.

In some embodiments, an isolated nucleic acids encoding one or more guide-RNA (multi-gRNA) expression cassette. In some embodiments, a multi-gRNA expression cassette comprises one or more Spacer (e.g., targeting sequences, guide sequences, seed sequences, etc.). A "spacer" refers to a nucleic acid sequence that specifically binds (e.g., hybridizes) to or shares a region of complementarity with a target sequence. A spacer sequence may comprise between 5 and 50 nucleotides (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides). In some embodiments, a spacer sequence comprises between 19 and 31 nucleotides. In some embodiments, a spacer sequence comprises 21, 22, or 23 nucleotides. In some embodiments, a multi-gRNA expression cassette comprises one or more spacer sequences that target (e.g., hybridize to or specifically bind to) one or more genes associated with Hurler Syndrome (e.g., IDUA gene). In some embodiments, a multi-gRNA comprises one or more linking sequences (e.g., a linking polynucleotide). In some embodiments, the one or more linking sequences comprises one or more restriction endonuclease cleavage sites. In some embodiments, the cleavage sites are recognized by restriction endonucleases that create blunt-ended fragments. Examples of restriction endonucleases include BbsI, BsaI, LguI, etc. Any of the promoter and/or regulatory sequences described herein can be incorporated into the isolated nucleic acid encoding one or more gRNAs. In some embodiments, the isolated nucleic acid for delivering the gRNA is an AAV vector. In some embodiments, the isolated nucleic acid for delivering the gRNA is a self-complementary AAV vector. In some embodiments, the gRNA can be delivered to the cell or subject using any suitable known method in the art, e.g., direct delivery by transfection, other viral platform such as lentivirus, adenovirus, HSV, ceDNA, retrovirus, liposome, nanoparticle, etc.).

Recombinant Adeno-Associated Viruses (rAAVs) and Other Vectors

Aspects of the disclosure relate to vectors comprising an isolated nucleic acid comprising an expression cassette encoding (i) a first region comprising a catalytically inactive dCas13b protein; (ii) a second region comprising a first signal sequence; (iii) a third region comprising an Adenosine Deaminase Acting on RNA deaminase domain (ADARdd); and (iv) a fourth region comprising a second signal sequence. In some embodiments, an RGN and a multi-gRNA are encoded by a single isolated nucleic acid. In some embodiments, an RGN is encoded by a vector and a multi-gRNA is encoded by a second (e.g., separate) vector. As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. In some embodiments, a vector is a viral vector, such as an rAAV vector, a lentiviral vector, an adenoviral vector, a retroviral vector, etc. Thus, the term includes cloning and expression vehicles, as well as viral vectors. In some embodiments, useful vectors are contemplated to be those vectors in which the nucleic acid segment to be transcribed is positioned under the transcriptional control of a promoter.

In some aspects, the disclosure provides isolated adeno-associated viruses (AAVs). As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a transgene of the rAAV will be delivered specifically to one or more predetermined tissue(s) (e.g., ocular tissues, neurons, liver, etc.). The AAV capsid is an important element in determining these tissue-specific targeting capabilities (e.g., tissue tropism). Thus, an rAAV having a capsid appropriate for the tissue being targeted can be selected.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an AAV capsid protein has a tropism for liver tissue (e.g., hepatocytes, etc.). In some embodiments, an AAV capsid protein does not target neuronal cells. In some embodiments, an AAV capsid protein does not cross the blood-brain barrier (BBB).

In some embodiments, an AAV capsid protein is of an AAV serotype selected from the group consisting of AAV1, AAV2, AAV3, AAV4, AAV5, AAV6, AAV7, AAV8, AAV9, AAV9.hr, AAVrh8, AAVrh10, AAVrh39, AAVrh43, AAV.PHP.B, AAV.PHP.eB, and variants of any of the foregoing. In some embodiments, an AAV capsid protein is of a serotype derived from a non-human primate, for example AAVrh8 serotype. In some embodiments, the AAV capsid protein is an AAV8 capsid protein.

In some embodiments, an rAAV vector or rAAV particle comprises a mutant ITR that lacks a functional terminal resolution site (TRS). The term "lacking a terminal resolution site" can refer to an AAV ITR that comprises a mutation (e.g., a sense mutation such as a non-synonymous mutation, or missense mutation) that abrogates the function of the terminal resolution site (TRS) of the ITR, or to a truncated AAV ITR that lacks a nucleic acid sequence encoding a functional TRS (e.g., a ΔTRS ITR). Without wishing to be bound by any particular theory, a rAAV vector comprising an ITR lacking a functional TRS produces a self-complementary rAAV vector, for example as described by McCarthy (2008) *Molecular Therapy* 16 (10): 1648-1656.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the disclosure relates to a host cell containing a nucleic acid that comprises an expression encoding (i) a first region comprising a catalytically inactive dCas13b protein; (ii) a second region comprising a first signal sequence; (iii) a third region comprising an Adenosine Deaminase Acting on RNA deaminase domain (ADARdd); and (iv) a fourth region comprising a second signal sequence. A "host cell" refers to any cell that harbors, or is capable of harboring, a substance of interest. Often a host cell is a mammalian cell. In some embodiments, a host cell is a neuron. In some embodiments, a host cell is a photoreceptor cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation. In some embodiments, the host cell is a mammalian cell, a yeast cell, a bacterial cell, an insect cell, a plant cell, or a fungal cell. In some embodiments, the host cell is a hepatocyte.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the disclosure. See, e.g., K. Fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an AAV vector (comprising a transgene flanked by ITR elements) to be packaged into AAV particles, an AAV helper function vector, and an accessory function vector. An AAV helper function vector encodes the "AAV helper function" sequences (e.g., rep and cap), which function in trans for productive AAV replication and encapsidation. Preferably, the AAV helper function vector supports efficient AAV vector production without generating any detectable wild-type AAV virions (e.g., AAV virions containing functional rep and cap genes). Non-limiting examples of vectors suitable for use with the disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (e.g., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpes virus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology,* 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous nucleic acids, such as a nucleotide integration vector and other nucleic acid molecules, into suitable host cells.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

Methods

Methods for delivering a transgene (e.g., an isolated nucleic acid described herein) to a subject are provided by the disclosure. The methods typically involve administering to a subject an effective amount of an isolated nucleic acid encoding the transgene(s). In some embodiments, expression constructs described by the disclosure are useful for base editing in a cell or a subject. In some embodiments, expression constructs described by the disclosure are useful for treating diseases characterized by one or more G to A substitution in a gene of interest in a subject. Non-limiting examples of diseases associated with one or more G to A substitution include TP53 W53X (e.g., 158G>A) associated with cancer, IDUA W402X (e.g., TGG>TAG mutation in exon 9) associated with Mucopolysaccharidosis type I (MPS I), COL3A1 W1278X (e.g., 3833G>A mutation) associated with Ehlers-Danlos syndrome, BMPR2 W298X (e.g., 893G>A) associated with primary pulmonary hypertension, AHI1 W725X (e.g., 2174G>A) associated with Joubert syndrome, FANCC W506X (e.g., 1517G>A) associated with Fanconi anemia, MYBPC3 W1098X (e.g., 3293G>A) associated with primary familial hypertrophic cardiomyopathy, and IL2RG W237X (e.g., 710G>A) associated with X-linked severe combined immunodeficiency. In some embodiments, the disease is Hurler syndrome. Hurler syndrome is the most severe form of mucopolysaccharidosis type 1 (MPS1), a rare lysosomal storage disease, characterized by skeletal abnormalities, cognitive impairment, heart disease, respiratory problems, enlarged liver and spleen, characteristic facies and reduced life expectancy. Hurler syndrome is caused by mutations in the Alpha-L-Iduronidase (IDUA) gene (4p16.3) leading to a complete deficiency in the alpha-L-iduronidase enzyme and lysosomal accumulation of dermatan sulfate and heparan sulfate. In some embodiments, the IDUA gene comprises a homozygous Idua-W402X mutation in human. In some embodiments, the IDUA gene comprises a homozygous Idua-W392X mutation in mouse.

In some embodiments, the method comprising administering to a subject in need thereof an effective amount of an isolated nucleic acid or an rAAV as described herein. A subject may be any mammalian organism, for example a human, non-human primate, horse, pig, dog, cat rodent, etc. In some embodiments a subject is a human.

An "effective amount" of a substance is an amount sufficient to produce a desired effect. In some embodiments, an effective amount of an isolated nucleic acid is an amount sufficient to transfect (or infect in the context of rAAV mediated delivery) a sufficient number of target cells of a target tissue of a subject. In some embodiments, a target tissue is CNS tissue (e.g., neurons, etc.) or liver cells (hepatocytes). In some embodiments, an effective amount of an isolated nucleic acid (e.g., which may be delivered via an rAAV) may be an amount sufficient to have a therapeutic benefit in a subject, e.g., to correct the G to A substitution in a target gene, for example, the IDUA gene, etc.), to extend the lifespan of a subject, to improve in the subject one or more symptoms of disease (e.g., a symptom of Hurler syndrome), etc. The effective amount will depend on a variety of factors such as, for example, the species, age, weight, health of the subject, and the tissue to be targeted, and may thus vary among subject and tissue as described elsewhere in the disclosure.

As used herein, the term "treating" refers to the application or administration of a composition encoding a transgene(s) to a subject, who has a genetic disorder caused by a G to A mutation in a responsible gene (e.g., IDUA gene for Hurler syndrome), with the purpose to cure, heal, alleviate, relieve, alter, remedy, ameliorate, improve, or affect the disorder, or the symptom of the disease. In some embodiments, the administration of a composition described herein increases a responsible gene (e.g., IDUA gene) expression level and/or activity by 2%, 5%, 10%, 20%, 30%, 40%, 50%, 60%, 70%, 80%, 90%, or 100% compared to a reference value. Methods of measuring gene (e.g., IDUA gene) expression level and/or activity are known in the art. Non-limiting exemplary reference value can be gene (e.g., IDUA gene) expression and/or activity of the same subject prior to receiving the treatment.

Alleviating a disease includes delaying the development or progression of the disease, or reducing disease severity. Alleviating the disease does not necessarily require curative results. As used therein, "delaying" the development of a disease (such as Hurler syndrome) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a disease includes initial onset and/or recurrence.

The isolated nucleic acids and rAAVs of the disclosure may be delivered to a subject in compositions according to any appropriate methods known in the art. For example, an rAAV, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments a host animal does not include a human.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue.

The compositions of the disclosure may comprise an rAAV alone, or in combination with one or more other viruses (e.g., a second rAAV encoding having one or more guide RNAs). In some embodiments, a composition comprises 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intracerebroventricular, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about 109 to 1016 genome copies. In some cases, a dosage between about 1011 to 1013 rAAV genome copies is appropriate. In certain embodiments, 1012 or 1013 rAAV genome copies is effective to target CNS tissue or liver tissue. In some cases, stable transgenic animals are produced by multiple doses of an rAAV.

In some embodiments, a dose of rAAV is administered to a subject no more than once per calendar day (e.g., a 24-hour period). In some embodiments, a dose of rAAV is administered to a subject no more than once per 2, 3, 4, 5, 6, or 7 calendar days. In some embodiments, a dose of rAAV is administered to a subject no more than once per calendar week (e.g., 7 calendar days). In some embodiments, a dose of rAAV is administered to a subject no more than bi-weekly (e.g., once in a two-calendar week period). In some embodiments, a dose of rAAV is administered to a subject no more than once per calendar month (e.g., once in 30 calendar days). In some embodiments, a dose of rAAV is administered to a subject no more than once per six calendar months. In some embodiments, a dose of rAAV is administered to a subject no more than once per calendar year (e.g., 365 days or 366 days in a leap year).

In some embodiments, rAAV compositions are formulated to reduce aggregation of AAV particles in the composition, particularly where high rAAV concentrations are present (e.g., ~1013 GC/ml or more). Methods for reducing aggregation of rAAVs are well known in the art and include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated.

In addition to the methods of delivery described above, the following techniques are also contemplated as alternative methods of delivering the rAAV compositions to a host. Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

EXAMPLES

Example 1

Microbial Cas13 proteins are RNA-guided RNA nucleases. The catalytically deficient version of Cas13 (dCas13) can serve as a platform for targeted RNA binding, and enable RNA base editing by coupling with an RNA-modifying enzyme. RNA base editing has several advantages as a therapeutic approach. First, it is independent of endogenous DNA repair mechanisms that limit some genome editing strategies such as homology-directed repair, and therefore can function in a broader range of cells. Second, whereas DNA base editing involving other Cas effectors relies on a suitable protospacer-adjacent motif (PAM) in the target DNA, dCas13-mediated RNA base editing has a much more relaxed constraint on the target nucleic acid sequence context. Furthermore, RNA editing does not permanently alter the genetic information, and therefore has a potentially less concerning safety profile as a gene therapy approach.

RNA editing tools comprising dCas13 fused with Adenosine Deaminase Acting on RNA deaminase domain (ADARdd) have been previously described, and convert an adenosine (A) to an inosine (I) that is functionally read as guanosine (G) by various cellular processes such as translation. The dCas13-ADARdd has been shown as an efficient RNA base editor in mammalian cell culture. However, the in vivo editing efficiency and therapeutic efficacy remain to be studied. This example describes dCas13-ADARdd reagents that are amenable to AAV vector-mediated gene delivery. The effectiveness of the rAAV vectors was examined in correcting a disease-associated mutation in mice. Several parameters were investigated in the context of RNA editing efficiency (e.g., using a reporter assay in HEK293FT cells), for example Cas13 orthologues, ADARdd variants, fusion orientations, subcellular localization signals, gRNA designs, and promoters. Robust editing was observed by the rAAV vectors. Editing of endogenous transcripts and disease-related RNA targets in cell lines was also efficient. Selected editors were packaged into AAV particles (rAAVs) and systemically delivered to a mouse model of Hurler syndrome that harbors a homozygous Idua-W392X mutation (e.g., UGG to UAG) that is analogous to the most common mutation in human patients. Five weeks later, liver total RNA was extracted and subjected to reverse transcription and PCR amplification. Deep sequencing of targeted Idua amplicon indicated that corrected transcript accounted for up to 15% of total Idua mRNA with minimal by-stander editing. The IDUA activity in liver lysate was restored to about 1% of the normal level, surpassing the targeted therapeutic threshold of 0.5%.

Example 2

Cas13 proteins are RNA-guided RNA nucleases. The catalytically deficient version of Cas13 (dCas13) can serve as a platform for targeted RNA binding, and enable RNA base editing by coupling with an RNA-modifying enzyme (e.g., Adenosine Deaminase Acting on RNA deaminase domain (ADARdd)). RNA base editing is advantageous as a therapeutic approach in that it is independent of endogenous DNA repair mechanisms that limit genome editing strategies, and therefore can function in a broader range of cells. Further, whereas DNA base editing involving other Cas effectors relies on a suitable protospacer-adjacent motif (PAM) in the target DNA, dCas13-mediated RNA base editing has a much more relaxed constraint on the target nucleic acid sequence context. Moreover, RNA editing does not permanently alter the genetic information, and therefore has a potentially less concerning safety profile as a gene therapy approach.

Currently available RNA editing tools comprising dCas13 fused with Adenosine Deaminase Acting on RNA deaminase domain (ADARdd), which is capable of converting an adenosine (A) to an inosine (I) that is functionally read as guanosine (G) by various cellular processes such as translation. A potentially broad therapeutic application is to correct pathogenic missense mutations and nonsense mutations (PTC; UAA, UAG, or UGA) caused by a G to A base change. The dCas13-ADARdd has been shown as an efficient RNA base editor in mammalian cell culture. However, currently available dCas13-ADARdd fusion proteins cannot be packaged into a single AAV genome for gene delivery in vivo due to the large size of the fusion protein. (FIG. 1A) Therefore, the in vivo editing efficiency and therapeutic efficacy of the dCas13 mediated RNA base editors remain elusive.

In the present disclosure, dCas13-ADARdd base editors were designed such that they are amenable to AAV vector-mediated gene delivery. Their effectiveness in correcting a disease-associated mutation in mice was evaluated.

Figure 1B:
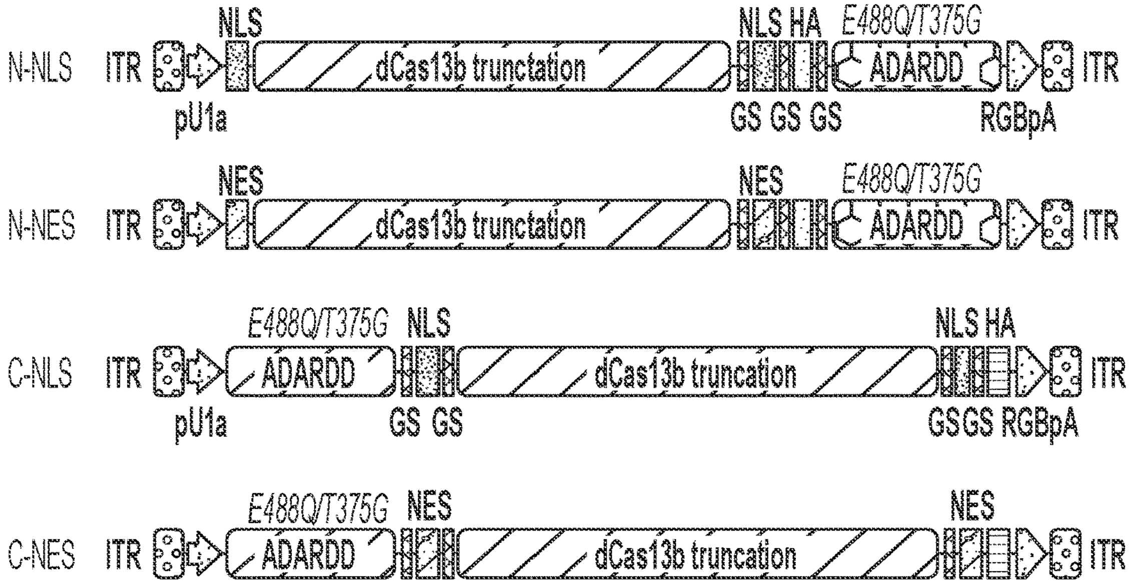
Figure 1C:
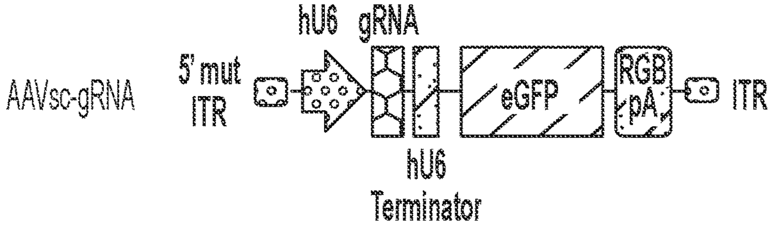

Several parameters for RNA editing were considered for the design of the base editors, including Cas13 orthologues, ADARdd variants, fusion orientations, subcellular localization signals, gRNA designs, and promoters were optimized. The differences between previously described base editors and the base editors described by the disclosure are shown in FIG. 1B. The present base editors adopted a shorter promoter (e.g., ula), rather than the conventional CMV promoter. A truncated version of dCas13b was included. The truncated dCas13b can either be fused to the N-terminus or the C-terminus of the ADARdd. Mutant versions of ADARdd (e.g., ADARdd with E488Q/T375G double mutations) were used in the constructs. The dCas13 protein is fused to ADARdd protein by (GS) n links. Subcellular localization signals (e.g., nuclear export signals (NES) or nuclear localization signals (NLS)) were added to either the C-terminal or N-terminal of the protein coding sequences. In some embodiments, a hemagglutinin (HA) tag is included in the constructs to facilitate detection. The schematic designs of the present AAV base editors vectors are shown in FIG. 1C (SEQ ID NOs: 5-8).

Figure 2A:
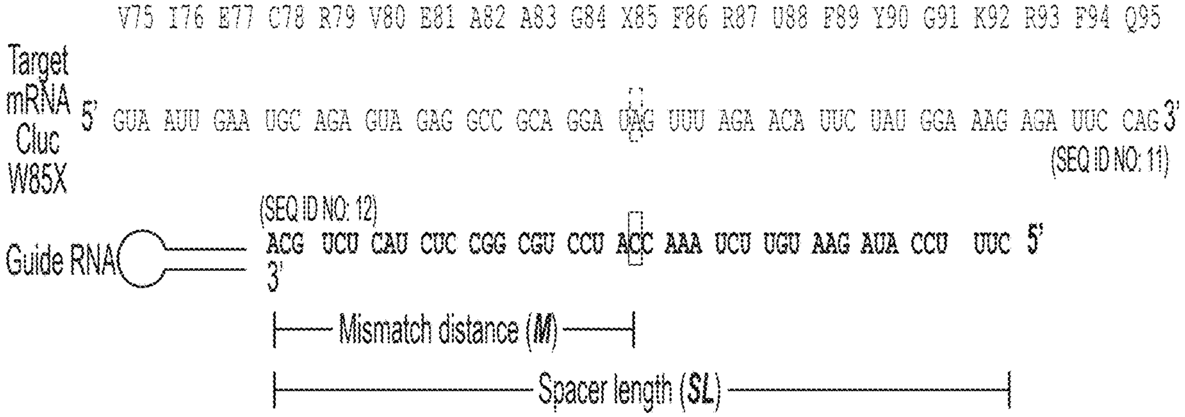
FIGS. 2A-2B are graphs showing the representative data for the dCas13-ADARdd editors in correcting W85X mutation using the Cluc W85X reporter in HEK293FT cells.
Figure 2B:
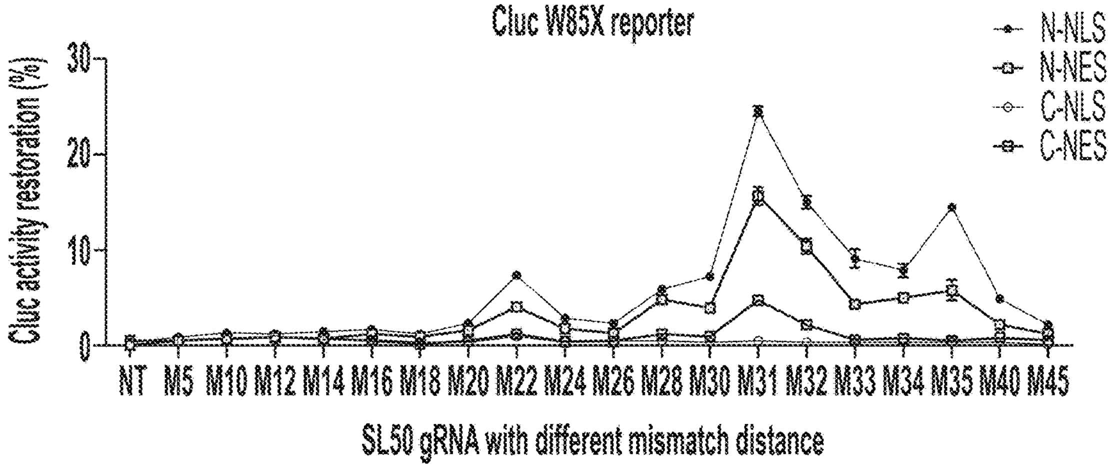

The rAAV vectors were tested for their base editing abilities in vitro using a Cluc W85X reporter construct in H293FT cells. The W85X reporter carries an G to A mutation which results in a premature stop codon at position W95. In this assay, if the W85X mutation was corrected by the base editors, an increase in Cluc activity should be observed. Indeed, robust editing was observed in AAV base editors constructs where the NES or NLS were placed at the N terminal of the protein coding sequences (FIG. 2B). The base editor with the NES placed at the C terminal of the protein coding sequences showed moderate RNA editing effect, while the base editor having the NLS placed at the C terminal of the protein coding sequences showed almost no RNA editing effect. RNA Editing of endogenous transcripts and disease-related RNA targets in cell lines was also efficient.

Figure 3A:
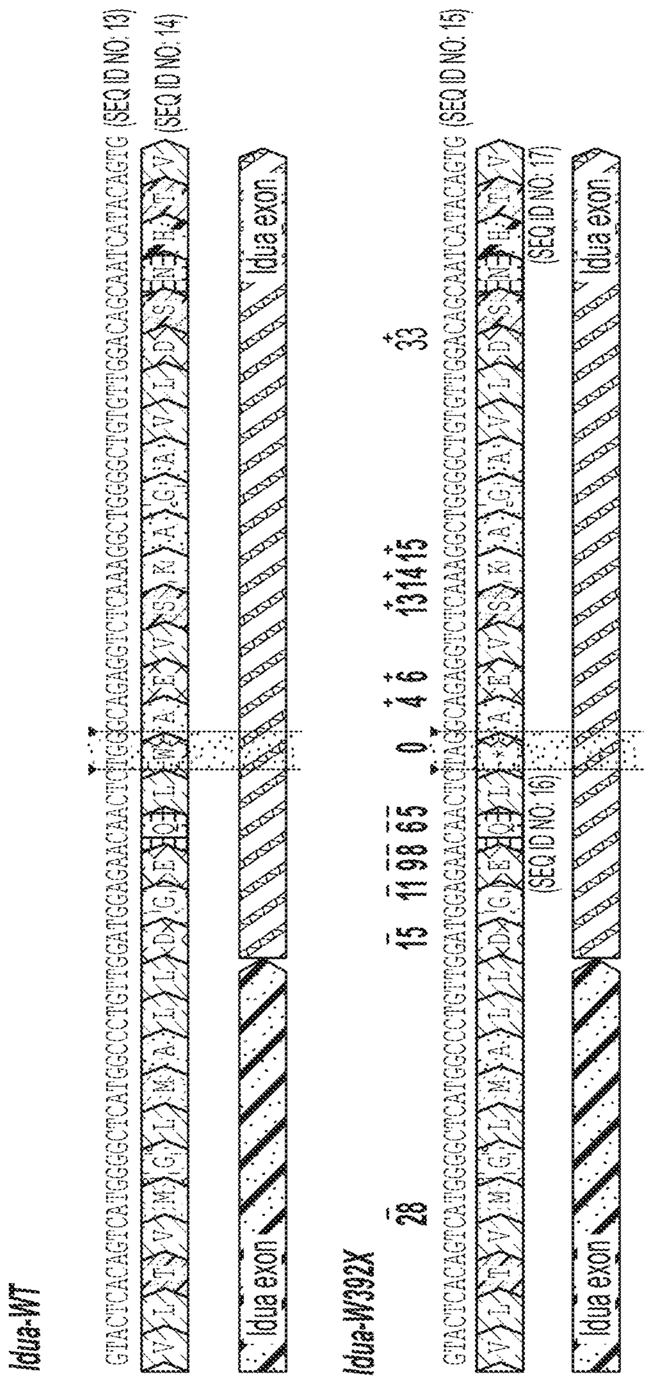
FIGS. 3A-3C are graphs showing in vivo correction of Idua-W392X mutation in mice by AAV-dCas13-ADARdd editors.
Figure 3B:
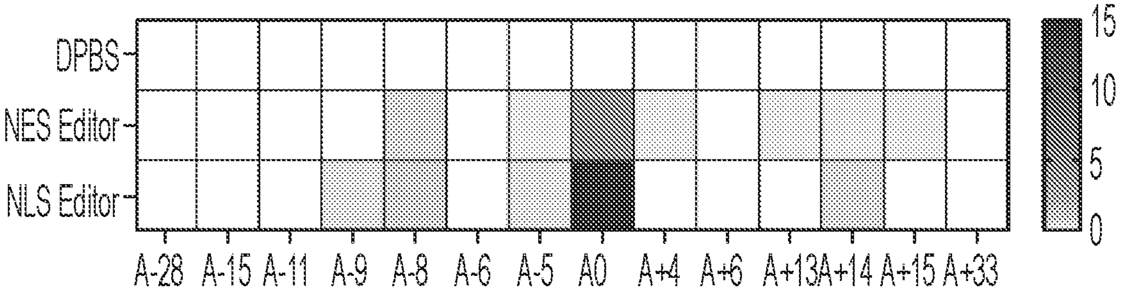
Figure 3C:
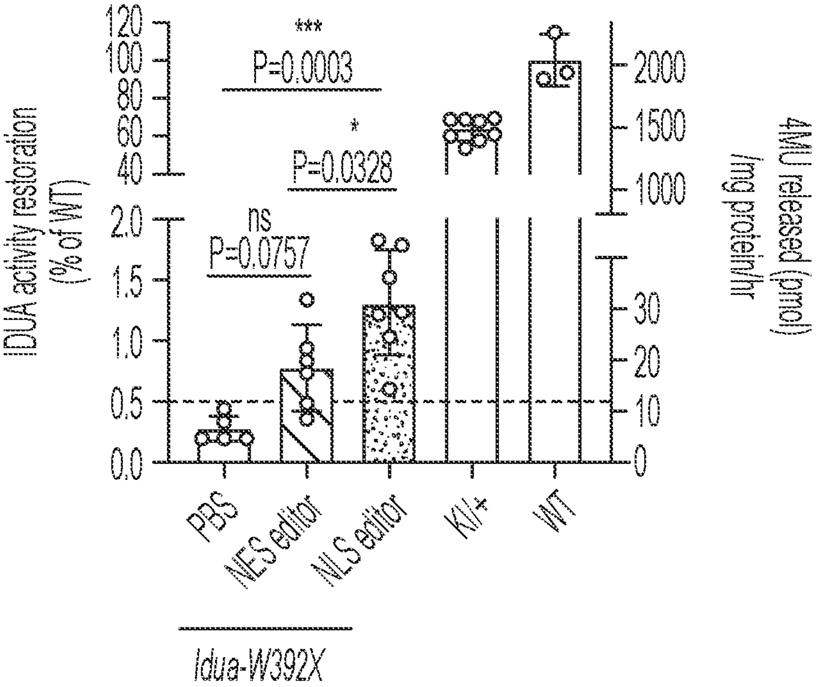
Figure 4A:
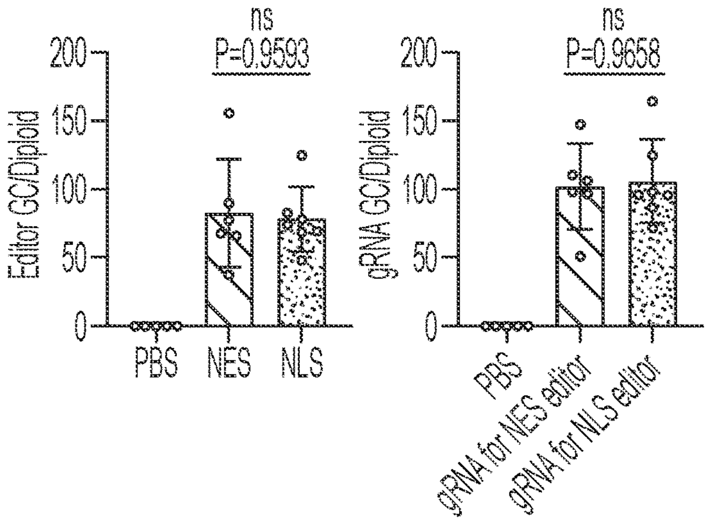
FIGS. 4A-4D show that in vivo therapeutic efficacy is positively correlated with editor and gRNA gene delivery efficiency.
Figure 4B:
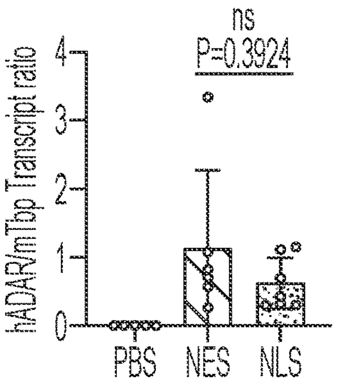
Figure 4C:
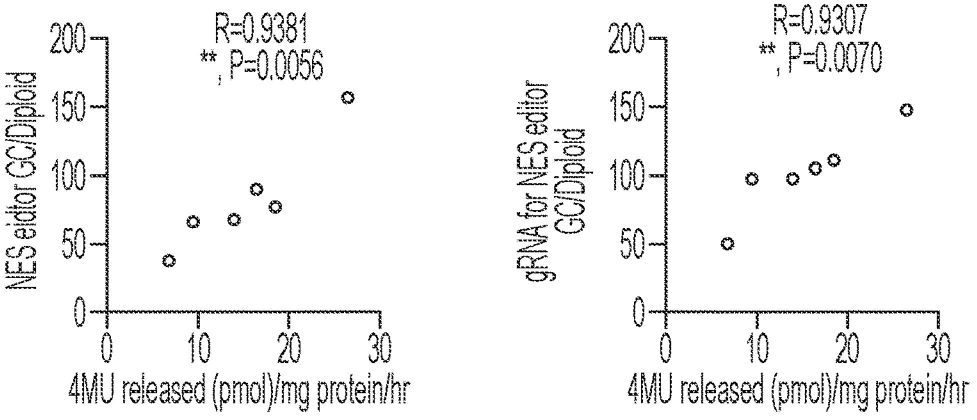
Figure 4D:
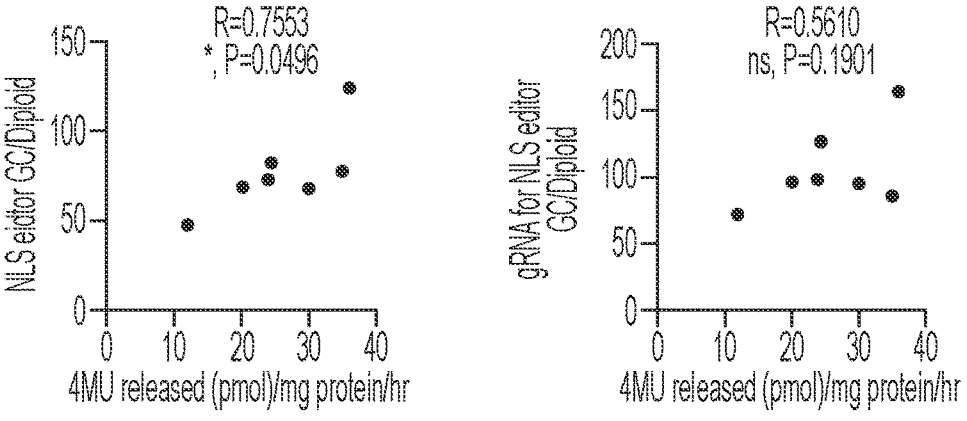

Selected editors (N-NLS and N-NES) were packaged into AAV vectors and delivered to a mouse model of Hurler syndrome via systemic injection. The Hurler Syndrome mice harbor a homozygous Idua-W392X mutation (UGG→UAG), which is analogous to the most common mutation in Hurler Syndrome patients (FIG. 3A). Five weeks later, liver total RNA was extracted and subjected to reverse transcription and PCR amplification. Deep sequencing of targeted Idua amplicon revealed that corrected transcript accounted for up to 15% of total Idua mRNA with minimal by-stander editing (FIG. 3B). The IDUA enzymatic activity in the liver lysate was restored above the therapeutic threshold of 0.5% of WT level. The NLS editor was more potent than the NES version regarding IDUA protein restoration (FIG. 3C), which is consistent with the results obtained using the in vitro reporter assay (FIG. 2B). Both editor versions yielded comparable vector genome copies (FIG. 4A) and editor mRNA levels (FIG. 4B) in the liver, indicating that the higher potency of NLS editor design was not due to higher gene delivery. By examining individual liver samples, it was observed that the in vivo therapeutic efficacy gauged by IDUA enzymatic activity restoration was positively correlated with editor and gRNA gene delivery efficiency (FIGS. 4C-4D).

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

SEQUENCES

In some embodiments, an isolated nucleic acid or vector (e.g., rAAV vector) described by the disclosure comprises or consists of a sequence set forth in any one of SEQ ID NOs: 1-10 In some embodiments, an isolated nucleic acid or vector (e.g., rAAV vector) described by the disclosure comprises or consists of a sequence set forth in any one of SEQ ID NOs: 1-10, wherein the sequence corresponding to a reporter protein (e.g., Guassia, Gluc, etc.) has been removed. In some embodiments, an isolated nucleic acid or vector (e.g., rAAV vector) described by the disclosure comprises or consists of a sequence that is complementary (e.g., the complement of) a sequence set forth in any one of SEQ ID NOs: 1-10. In some embodiments, an isolated nucleic acid or vector (e.g., rAAV vector) described by the disclosure comprises or consists of a sequence that is a reverse complement of a sequence set forth in any one of SEQ ID NOs: 1-10. In some embodiments, an isolated nucleic acid or vector (e.g., rAAV vector) described by the disclosure comprises or consists of a portion of a sequence set forth in any one of SEQ ID NOs: 1-10. A portion may comprise at least 25%, 50%, 60%, 70%, 80%, 90%, 95%, or 99% of a sequence set forth in any one of SEQ ID NOs: 1-10. In some embodiments, a nucleic acid sequence described by the disclosure is a nucleic acid sense strand (e.g., 5' to 3' strand), or in the context of a viral sequences a plus (+) strand. In some embodiments, a nucleic acid sequence described by the disclosure is a nucleic acid antisense strand (e.g., 3' to 5' strand), or in the context of viral sequences a minus (−) strand.

All NCBI Gene and Accession Number Sequences are incorporated herein by reference in their entireties.

The contents of the text file submitted electronically herewith are incorporated herein by reference in their entirety: A computer readable format copy of the Sequence Listing (filename: U0120.70139WO00-SEQ.txt, date recorded: Apr. 9, 2020, file size ~44,449 bytes).

>Amino acid sequence of Psp dead Cas13b protein (SEQ ID NO: 1)

NIPALVENQKKYFGTYSVMAMLNAQTVLDHIQKVADIEGEQNENNENLWFHPVMSHL

YNAKNGYDKQPEKTMFIIERLQSYFPFLKIMAENQREYSNGKYKQNRVEVNSNDIFEVL

KRAFGVLKMYRDLTNAYKTYEEKLNDGCEFLTSTEQPLSGMINNYYTVALRNMNERY

GYKTEDLAFIQDKRFKFVKDAYGKKKSQVNTGFFLSLQDYNGDTQKKLHLSGVGIALL

ICLFLDKQYINIFLSRLPIFSSYNAQSEERRIIIRSFGINSIKLPKDRIHSEKSNKSVAMDML

NEVKRCPDELFTTLSAEKQSRFRIISDDHNEVLMKRSSDRFVPLLLQYIDYGKLFDHIRF

HVNMGKLRYLLKADKTCIDGQTRVRVIEQPLNGFGRLEEAETMRKQENGTFGNSGIRIR

DFENMKRDDANPANYPYIVDTYTHYILENNKVEMFINDKEDSAPLLPVIEDDRYVVKTI

PSCRMSTLEIPAMAFHMFLFGSKKTEKLIVDVHNRYKRLFQAMQKEEVTAENIASFGIA

ESDLPQKILDLISGNAHGKDVDAFIRLTVDDMLTDTERRIKRFKDDRKSIRSADNKMGK

RGFKQISTGKLADFLAKDIVLFQPSVNDGENKITGLNYRIMQSAIAVYDSGDDYEAKQQ

FKLMFEKARLIGKGTTEPHPFLYKVFARSIPANAVEFYERYLIERKFYLTGLSNEIKKGN

RVDVPFIRRDQNKWKTPAMKTLGRIYSEDLPVELPRQMFDNEIKSHLKSLPQMEGIDFN

NANVTYLIAEYMKRVLDDDFQTFYQWNRNYRYMDMLKGEYDRKGSLQHCFTSVEER

EGLWKERASRTERYRKQASNKIRSNRQMRNASSEEIETILDKRLSNSRNEYQKSEKVIRR

YRVQDALLFLLAKKTLTELADFDGERFKLKEIMPDAEKGILSEIMPMSFTFEKGGKKYTI

TSEGMKLKNYGDFFVLASDKRIGNLLELVGSDIVSKED

>Amino acid sequence of human mutant ADAR2dd with E488Q/T375G mutations (SEQ ID NO: 2)

QLHLPQVLADAVSRLVLGKFGDLTDNFSSPHARRKVLAGVVMTTGTDVKDAKVISVST

GGKCINGEYMSDRGLALNDCHAEIISRRSLLRFLYTQLELYLNNKDDQKRSIFQKSERG

GFRLKENVQFHLYISTSPCGDARIFSPHEPILEEPADRHPNRKARGQLRTKIESGQGTIPV

RSNASIQTWDGVLQGERLLTMSCSDKIARWNVVGIQGSLLSIFVEPIYFSSIILGSLYHGD

HLSRAMYQRISNIEDLPPLYTLNKPLLSGISNAEARQPGKAPNFSVNWTVGDSAIEVINA

TTGKDELGRASRLCKHALYCRWMRVHGKVPSHLLRSKITKPNVYHESKLAAKEYQAA

KARLFTAFIKAGLGAWVEKPTEQDQFSLT

>nucleic acid sequence for nuclear export signal (NES)

(SEQ ID NO: 3)

CTTCAACTGCCTCCACTTGAAAGACTGACACTG

>nucleic acid sequence for nuclear localization signal (NLS)

(SEQ ID NO: 4)

CCTGCAGCTAAGCGGGTTAAGTTGGAT

>rAAV-C-NLS nucleic acid sequence (SEQ ID NO: 5)

cctgcaggcagctgcgcgctcgctcgctcactgaggccgcccgggcaaagcccgggcgtcgggcgacctttggtcgcccggcctcagt gagcgagcgagcgcgcagagagggagtggccaactccatcactaggggttcctgcggcctctagaatggaggcggtactatgtagatg agaattcaggagcaaactgggaaaagcaactgcttccaaatatttgtgatttttacagtgtagttttggaaaaactcttagcctaccaattcttct aagtgttttaaaatgtgggagccagtacacatgaagttatagagtgttttaatgaggcttaaatatttaccgtaactatgaaatgctacgcatatc atgctgttcaggctccgtggccacgcaactcatactaccggtgtcgacgccaccatgcagctgcatttaccgcaggttttagctgacgctgtc tcacgcctggtcctgggtaagtttggtgacctgaccgacaacttctcctcccctcacgctcgcagaaaagtgctggctggagtcgtcatgac aacaggcacagatgttaaagatgccaaggtgataagtgtttctacaggaggcaaatgtattaatggtgaatacatgagtgatcgtggccttgc attaaatgactgccatgcagaaataatatctcggagatccttgctcagatttctttatacacaacttgagctttacttaaataacaaagatgatcaa aaaagatccatctttcagaaatcagagcgagggggtttaggctgaaggagaatgtccagtttcatctgtacatcagcacctctccctgtgga gatgccagaatcttctcaccacatgagccaatcctggaagaaccagcagatagacacccaaatcgtaaagcaagaggacagctacggac -continued caaaatagagtctggtcaggggacgattccagtgcgctccaatgcgagcatccaaacgtgggacggggtgctgcaaggggagcggctg ctcaccatgtcctgcagtgacaagattgcacgctggaacgtggtgggcatccagggatcactgctcagcattttcgtggagcccatttacttc tcgagcatcatcctgggcagcctttaccacggggaccacctttccagggccatgtaccagcggatctccaacatagaggacctgccacctc tctacaccctcaacaagcctttgctcagtggcatcagcaatgcagaagcacggcagccagggaaggcccccaacttcagtgtcaactgga cggtaggcgactccgctattgaggtcatcaacgccacgactgggaaggatgagctgggccgcgcgtcccgcctgtgtaagcacgcgttg tactgtcgctggatgcgtgtgcacggcaaggttccctcccacttactacgctccaagattaccaagcccaacgtgtaccatgagtccaagct ggcggcaaaggagtaccaggccgccaaggcgcgtctgttcacagccttcatcaaggcggggctgggggcctgggtggagaagcccac cgagcaggaccagttctcactcacgggatcccctgcagctaagcgggttaagttggatggatccaacatccccgctctggtggaaaacca gaagaagtactttggcacctacagcgtgatggccatgctgaacgctcagaccgtgctggaccacatccagaaggtggccgatattgaggg cgagcagaacgagaacaacgagaatctgtggtttcaccccgtgatgagccacctgtacaacgccaagaacggctacgacaagcagccc gagaaaaccatgttcatcatcgagcggctgcagagctacttcccattcctgaagatcatggccgagaaccagagagagtacagcaacggc aagtacaagcagaaccgcgtggaagtgaacagcaacgacatcttcgaggtgctgaagcgcgccttcggcgtgctgaagatgtacaggga cctgaccaacgcatacaagacctacgaggaaaagctgaacgacggctgcgagttcctgaccagcacagagcaacctctgagcggcatg atcaacaactactacacagtggccctgcggaacatgaacgagagatacggctacaagacagaggacctggccttcatccaggacaagcg gttcaagttcgtgaaggacgcctacggcaagaaaaagtcccaagtgaataccggattcttcctgagcctgcaggactacaacggcgacac acagaagaagctgcacctgagcggagtgggaatcgccctgctgatctgcctgttcctggacaagcagtacatcaacatctttctgagcagg ctgcccatcttctccagctacaatgcccagagcgaggaacggcggatcatcatcagatccttcggcatcaacagcatcaagctgcccaag gaccggattcacagcgagaagtccaacaagagcgtggccatggatatgctcaacgaagtgaagcggtgccccgacgagctgttcacaac actgtctgccgagaagcagtcccggttcagaatcatcagcgacgaccacaatgaagtgctgatgaagcggagcagcgacagattcgtgc ctctgctgctgcagtatatcgattacggcaagctgttcgaccacatcaggttccacgtgaacatgggcaagctgagatacctgctgaaggcc gacaagacctgcatcgacggccagaccagagtcagagtgatcgagcagcccctgaacggcttcggcagactggaagaggccgagaca atgcggaagcaagagaacggcaccttcggcaacagcggcatccggatcagagacttcgagaacatgaagcgggacgacgccaatcct gccaactatccctacatcgtggacacctacacacactacatcctggaaaacaacaaggtcgagatgtttatcaacgacaaagaggacagc gccccactgctgcccgtgatcgaggatgatagatacgtggtcaagacaatccccagctgccggatgagcaccctggaaattccagccatg gccttccacatgtttctgttcggcagcaagaaaaccgagaagctgatcgtggacgtgcacaaccggtacaagagactgttccaggccatgc agaaagaagaagtgaccgccgagaatatcgccagcttcggaatcgccgagagcgacctgcctcagaagatcctggatctgatcagcggc aatgcccacggcaaggatgtggacgccttcatcagactgaccgtggacgacatgctgaccgacaccgagcggagaatcaagagattcaa ggacgaccggaagtccattcggagcgccgacaacaagatgggaaagagaggcttcaagcagatctccacaggcaagctggccgacttc ctggccaaggacatcgtgctgtttcagcccagcgtgaacgatggcgagaacaagatcaccggcctgaactaccggatcatgcagagcgc cattgccgtgtacgatagcggcgacgattacgaggccaagcagcagttcaagctgatgttcgagaaggcccggctgatcggcaagggca caacagagcctcatccatttctgtacaaggtgttcgcccgcagcatccccgccaatgccgtcgagttctacgagcgctacctgatcgagcg gaagttctacctgaccggcctgtccaacgagatcaagaaaggcaacagagtggatgtgcccttcatccggcgggaccagaacaagtgga aaacacccgccatgaagaccctgggcagaatctacagcgaggatctgcccgtggaactgcccagacagatgttcgacaatgagatcaag tcccacctgaagtccctgccacagatggaaggcatcgacttcaacaatgccaacgtgacctatctgatcgccgagtacatgaagagagtgc tggacgacgacttccagaccttctaccagtggaaccgcaactaccggtacatggacatgcttaagggcgagtacgacagaaagggctccc tgcagcactgcttcaccagcgtggaagagagagaaggcctctggaaagagcgggcctccagaacagagcggtacagaaagcaggcca gcaacaagatccgcagcaaccggcagatgagaaacgccagcagcgaagagatcgagacaatcctggataagcggctgagcaacagc cggaacgagtaccagaaaagcgagaaagtgatccggcgctacagagtgcaggatgccctgctgtttctgctggccaaaaagaccctgac cgaactggccgatttcgacggcgagaggttcaaactgaaagaaatcatgcccgacgccgagaagggaatcctgagcgagatcatgccca tgagcttcaccttcgagaaaggcggcaagaagtacaccatcaccagcgagggcatgaagctgaagaactacggcgacttctttgtgctgg -continued ctagcgacaagaggatcggcaacctgctggaactcgtgggcagcgacatcgtgtccaaagaggatggatcccctgcagctaagcgggtt aagttggatggatcctacccatacgatgttccagattacgcttaaaagcttgaattcgatctttttccctctgccaaaaattatggggacatcatg aagccccttgagcatctgacttctggctaataaaggaaatttattttcattgcaatagtgtgttggaattttttgtgtctctcactcggcggccgca ggaacccctagtgatggagttggccactccctctctgcgcgctcgctcgctcactgaggccgggcgaccaaaggtcgcccgacgcccgg gctttgcccgggcggcctcagtgagcgagcgagcgcgcagctgcctgcagg >rAAV-N-NLS nucleic acid sequence (SEQ ID NO: 6)

cctgcaggcagctgcgcgctcgctcgctcactgaggccgcccgggcaaagcccgggcgtcgggcgacctttggtcgcccggcctcagt gagcgagcgagcgcgcagagagggagtggccaactccatcactaggggttcctgcggcctctagaatggaggcggtactatgtagatg agaattcaggagcaaactgggaaaagcaactgcttccaaatatttgtgatttttacagtgtagttttggaaaaactcttagcctaccaattcttct aagtgttttaaaatgtgggagccagtacacatgaagttatagagtgttttaatgaggcttaaatatttaccgtaactatgaaatgctacgcatatc atgctgttcaggctccgtggccacgcaactcatactaccggtgtcgacgccaccatgcctgcagctaagcgggttaagttggataacatccc cgctctggtggaaaaccagaagaagtactttggcacctacagcgtgatggccatgctgaacgctcagaccgtgctggaccacatccagaa ggtggccgatattgagggcgagcagaacgagaacaacgagaatctgtggtttcaccccgtgatgagccacctgtacaacgccaagaacg gctacgacaagcagcccgagaaaaccatgttcatcatcgagcggctgcagagctacttcccattcctgaagatcatggccgagaaccaga gagagtacagcaacggcaagtacaagcagaaccgcgtggaagtgaacagcaacgacatcttcgaggtgctgaagcgcgccttcggcgt gctgaagatgtacagggacctgaccaacgcatacaagacctacgaggaaaagctgaacgacggctgcgagttcctgaccagcacagag caacctctgagcggcatgatcaacaactactacacagtggccctgcggaacatgaacgagagatacggctacaagacagaggacctggc cttcatccaggacaagcggttcaagttcgtgaaggacgcctacggcaagaaaaagtcccaagtgaataccggattcttcctgagcctgcag gactacaacggcgacacacagaagaagctgcacctgagcggagtgggaatcgccctgctgatctgcctgttcctggacaagcagtacat caacatctttctgagcaggctgcccatcttctccagctacaatgcccagagcgaggaacggcggatcatcatcagatccttcggcatcaaca gcatcaagctgcccaaggaccggattcacagcgagaagtccaacaagagcgtggccatggatatgctcaacgaagtgaagcggtgccc cgacgagctgttcacaacactgtctgccgagaagcagtcccggttcagaatcatcagcgacgaccacaatgaagtgctgatgaagcgga gcagcgacagattcgtgcctctgctgctgcagtatatcgattacggcaagctgttcgaccacatcaggttccacgtgaacatgggcaagctg agatacctgctgaaggccgacaagacctgcatcgacggccagaccagagtcagagtgatcgagcagcccctgaacggcttcggcagac tggaagaggccgagacaatgcggaagcaagagaacggcaccttcggcaacagcggcatccggatcagagacttcgagaacatgaagc gggacgacgccaatcctgccaactatccctacatcgtggacacctacacacactacatcctggaaaacaacaaggtcgagatgtttatcaa cgacaaagaggacagcgccccactgctgcccgtgatcgaggatgatagatacgtggtcaagacaatccccagctgccggatgagcacc ctggaaattccagccatggccttccacatgtttctgttcggcagcaagaaaaccgagaagctgatcgtggacgtgcacaaccggtacaaga gactgttccaggccatgcagaaagaagaagtgaccgccgagaatatcgccagcttcggaatcgccgagagcgacctgcctcagaagatc ctggatctgatcagcggcaatgcccacggcaaggatgtggacgccttcatcagactgaccgtggacgacatgctgaccgacaccgagcg gagaatcaagagattcaaggacgaccggaagtccattcggagcgccgacaacaagatgggaaagagaggcttcaagcagatctccaca ggcaagctggccgacttcctggccaaggacatcgtgctgtttcagcccagcgtgaacgatggcgagaacaagatcaccggcctgaacta ccggatcatgcagagcgccattgccgtgtacgatagcggcgacgattacgaggccaagcagcagttcaagctgatgttcgagaaggccc ggctgatcggcaagggcacaacagagcctcatccatttctgtacaaggtgttcgcccgcagcatccccgccaatgccgtcgagttctacga gcgctacctgatcgagcggaagttctacctgaccggcctgtccaacgagatcaagaaaggcaacagagtggatgtgcccttcatccggcg ggaccagaacaagtggaaaacacccgccatgaagaccctgggcagaatctacagcgaggatctgcccgtggaactgcccagacagatg ttcgacaatgagatcaagtcccacctgaagtccctgccacagatggaaggcatcgacttcaacaatgccaacgtgacctatctgatcgccg agtacatgaagagagtgctggacgacgacttccagaccttctaccagtggaaccgcaactaccggtacatggacatgcttaagggcgagt acgacagaaagggctccctgcagcactgcttcaccagcgtggaagagagagaaggcctctggaaagagcgggcctccagaacagagc ggtacagaaagcaggccagcaacaagatccgcagcaaccggcagatgagaaacgccagcagcgaagagatcgagacaatcctggat aagcggctgagcaacagccggaacgagtaccagaaaagcgagaaagtgatccggcgctacagagtgcaggatgccctgctgtttctgct -continued ggccaaaaagaccctgaccgaactggccgatttcgacggcgagaggttcaaactgaaagaaatcatgcccgacgccgagaagggaatc
ctgagcgagatcatgcccatgagcttcaccttcgagaaaggcggcaagaagtacaccatcaccagcgagggcatgaagctgaagaacta
cggcgacttctttgtgctggctagcgacaagaggatcggcaacctgctggaactcgtgggcagcgacatcgtgtccaaagaggatggatc
ccctgcagctaagcgggttaagttggatggatcctacccatacgatgttccagattacgctggatcccagctgcatttaccgcaggttttagct
gacgctgtctcacgcctggtcctgggtaagtttggtgacctgaccgacaacttctcctcccctcacgctcgcagaaaagtgctggctggagt
cgtcatgacaacaggcacagatgttaaagatgccaaggtgataagtgtttctacaggaggcaaatgtattaatggtgaatacatgagtgatc
gtggccttgcattaaatgactgccatgcagaaataatatctcggagatccttgctcagatttctttatacacaacttgagctttacttaaataacaa
agatgatcaaaaaagatccatctttcagaaatcagagcgaggggggtttaggctgaaggagaatgtccagtttcatctgtacatcagcacct
ctccctgtggagatgccagaatcttctcaccacatgagccaatcctggaagaaccagcagatagacacccaaatcgtaaagcaagaggac
agctacggaccaaaatagagtctggtcaggggacgattccagtgcgctccaatgcgagcatccaaacgtgggacggggtgctgcaagg
ggagcggctgctcaccatgtcctgcagtgacaagattgcacgctggaacgtggtgggcatccagggatcactgctcagcattttcgtggag
cccatttacttctcgagcatcatcctgggcagcctttaccacggggaccacctttccagggccatgtaccagcggatctccaacatagagga
cctgccacctctctacaccctcaacaagcctttgctcagtggcatcagcaatgcagaagcacggcagccagggaaggcccccaacttcag
tgtcaactggacggtaggcgactccgctattgaggtcatcaacgccacgactgggaaggatgagctgggccgcgcgtcccgcctgtgtaa
gcacgcgttgtactgtcgctggatgcgtgtgcacggcaaggttccctcccacttactacgctccaagattaccaagcccaacgtgtaccatg
agtccaagctggcggcaaaggagtaccaggccgccaaggcgcgtctgttcacagccttcatcaaggcggggctgggggcctgggtgga
gaagcccaccgagcaggaccagttctcactcacgtaaaagcttgaattcgatctttttccctctgccaaaaattatggggacatcatgaagcc
ccttgagcatctgacttctggctaataaaggaaatttattttcattgcaatagtgtgttggaattttttgtgtctctcactcggcggccgcaggaac
ccctagtgatggagttggccactccctctctgcgcgctcgctcgctcactgaggccgggcgaccaaaggtcgcccgacgcccgggctttg
cccgggcggcctcagtgagcgagcgagcgcgcagctgcctgcagg >rAAV-C-NES nucleic acid sequence (SEQ ID NO: 7)

cctgcaggcagctgcgcgctcgctcgctcactgaggccgcccgggcaaagcccgggcgtcgggcgacctttggtcgcccggcctcagt
gagcgagcgagcgcgcagagagggagtggccaactccatcactaggggttcctgcggcctctagaatggaggcggtactatgtagatg
agaattcaggagcaaactgggaaaagcaactgcttccaaatatttgtgatttttacagtgtagttttggaaaaactcttagcctaccaattcttct
aagtgttttaaaatgtgggagccagtacacatgaagttatagagtgttttaatgaggcttaaatatttaccgtaactatgaaatgctacgcatatc
atgctgttcaggctccgtggccacgcaactcatactaccggtgtcgacgccaccatgcagctgcatttaccgcaggttttagctgacgctgtc
tcacgcctggtcctgggtaagtttggtgacctgaccgacaacttctcctcccctcacgctcgcagaaaagtgctggctggagtcgtcatgac
aacaggcacagatgttaaagatgccaaggtgataagtgtttctacaggaggcaaatgtattaatggtgaatacatgagtgatcgtggccttgc
attaaatgactgccatgcagaaataatatctcggagatccttgctcagatttctttatacacaacttgagctttacttaaataacaaagatgatcaa
aaaagatccatctttcagaaatcagagcgaggggggtttaggctgaaggagaatgtccagtttcatctgtacatcagcacctctccctgtgga
gatgccagaatcttctcaccacatgagccaatcctggaagaaccagcagatagacacccaaatcgtaaagcaagaggacagctacggac
caaaatagagtctggtcaggggacgattccagtgcgctccaatgcgagcatccaaacgtgggacggggtgctgcaaggggagcggctg
ctcaccatgtcctgcagtgacaagattgcacgctggaacgtggtgggcatccagggatcactgctcagcattttcgtggagcccatttacttc
tcgagcatcatcctgggcagcctttaccacggggaccacctttccagggccatgtaccagcggatctccaacatagaggacctgccacctc
tctacaccctcaacaagcctttgctcagtggcatcagcaatgcagaagcacggcagccagggaaggcccccaacttcagtgtcaactgga
cggtaggcgactccgctattgaggtcatcaacgccacgactgggaaggatgagctgggccgcgcgtcccgcctgtgtaagcacgcgttg
tactgtcgctggatgcgtgtgcacggcaaggttccctcccacttactacgctccaagattaccaagcccaacgtgtaccatgagtccaagct
ggcggcaaaggagtaccaggccgccaaggcgcgtctgttcacagccttcatcaaggcggggctgggggcctgggtggagaagcccac
cgagcaggaccagttctcactcacgggatcccttcaactgcctccacttgaaagactgacactgaacatccccgctctggtggaaaaccag
aagaagtactttggcacctacagcgtgatggccatgctgaacgctcagaccgtgctggaccacatccagaaggtggccgatattgagggc -continued gagcagaacgagaacaacgagaatctgtggtttcaccccgtgatgagccacctgtacaacgccaagaacggctacgacaagcagcccg agaaaaccatgttcatcatcgagcggctgcagagctacttcccattcctgaagatcatggccgagaaccagagagagtacagcaacggca agtacaagcagaaccgcgtggaagtgaacagcaacgacatcttcgaggtgctgaagcgcgccttcggcgtgctgaagatgtacagggac ctgaccaacgcatacaagacctacgaggaaaagctgaacgacggctgcgagttcctgaccagcacagagcaacctctgagcggcatgat caacaactactacacagtggccctgcggaacatgaacgagagatacggctacaagacagaggacctggccttcatccaggacaagcggt tcaagttcgtgaaggacgcctacggcaagaaaaagtcccaagtgaataccggattcttcctgagcctgcaggactacaacggcgacacac agaagaagctgcacctgagcggagtgggaatcgccctgctgatctgcctgttcctggacaagcagtacatcaacatctttctgagcaggct gcccatcttctccagctacaatgcccagagcgaggaacggcggatcatcatcagatccttcggcatcaacagcatcaagctgcccaagga ccggattcacagcgagaagtccaacaagagcgtggccatggatatgctcaacgaagtgaagcggtgccccgacgagctgttcacaacac tgtctgccgagaagcagtcccggttcagaatcatcagcgacgaccacaatgaagtgctgatgaagcggagcagcgacagattcgtgcctc tgctgctgcagtatatcgattacggcaagctgttcgaccacatcaggttccacgtgaacatgggcaagctgagatacctgctgaaggccga caagacctgcatcgacggccagaccagagtcagagtgatcgagcagcccctgaacggcttcggcagactggaagaggccgagacaat gcggaagcaagagaacggcaccttcggcaacagcggcatccggatcagagacttcgagaacatgaagcgggacgacgccaatcctgc caactatccctacatcgtggacacctacacacactacatcctggaaaacaacaaggtcgagatgtttatcaacgacaaagaggacagcgcc ccactgctgcccgtgatcgaggatgatagatacgtggtcaagacaatccccagctgccggatgagcaccctggaaattccagccatggcc ttccacatgtttctgttcggcagcaagaaaaccgagaagctgatcgtggacgtgcacaaccggtacaagagactgttccaggccatgcaga aagaagaagtgaccgccgagaatatcgccagcttcggaatcgccgagagcgacctgcctcagaagatcctggatctgatcagcggcaat gcccacggcaaggatgtggacgccttcatcagactgaccgtggacgacatgctgaccgacaccgagcggagaatcaagagattcaagg acgaccggaagtccattcggagcgccgacaacaagatgggaaagagaggcttcaagcagatctccacaggcaagctggccgacttcct ggccaaggacatcgtgctgtttcagcccagcgtgaacgatggcgagaacaagatcaccggcctgaactaccggatcatgcagagcgcca ttgccgtgtacgatagcggcgacgattacgaggccaagcagcagttcaagctgatgttcgagaaggcccggctgatcggcaagggcaca acagagcctcatccatttctgtacaaggtgttcgcccgcagcatccccgccaatgccgtcgagttctacgagcgctacctgatcgagcgga agttctacctgaccggcctgtccaacgagatcaagaaaggcaacagagtggatgtgcccttcatccggcgggaccagaacaagtggaaa acacccgccatgaagaccctgggcagaatctacagcgaggatctgcccgtggaactgcccagacagatgttcgacaatgagatcaagtc ccacctgaagtccctgccacagatggaaggcatcgacttcaacaatgccaacgtgacctatctgatcgccgagtacatgaagagagtgctg gacgacgacttccagaccttctaccagtggaaccgcaactaccggtacatggacatgcttaagggcgagtacgacagaaagggctccctg cagcactgcttcaccagcgtggaagagagagaaggcctctggaaagagcgggcctccagaacagagcggtacagaaagcaggccag caacaagatccgcagcaaccggcagatgagaaacgccagcagcgaagagatcgagacaatcctggataagcggctgagcaacagcc ggaacgagtaccagaaaagcgagaaagtgatccggcgctacagagtgcaggatgccctgctgtttctgctggccaaaaagaccctgacc gaactggccgatttcgacggcgagaggttcaaactgaaagaaatcatgcccgacgccgagaagggaatcctgagcgagatcatgcccat gagcttcaccttcgagaaaggcggcaagaagtacaccatcaccagcgagggcatgaagctgaagaactacggcgacttctttgtgctggc tagcgacaagaggatcggcaacctgctggaactcgtgggcagcgacatcgtgtccaaagaggatggatcccttcaactgcctccacttga aagactgacactgtacccatacgatgttccagattacgcttaaaagcttgaattcgatctttttccctctgccaaaaattatggggacatcatga agccccttgagcatctgacttctggctaataaaggaaatttattttcattgcaatagtgtgttggaattttttgtgtctctcactcggcggccgcag gaacccctagtgatggagttggccactccctctctgcgcgctcgctcgctcactgaggccgggcgaccaaaggtcgcccgacgcccggg ctttgcccgggcggcctcagtgagcgagcgagcgcgcagctgcctgcagg >rAAV-N-NES nucleic acid sequence (SEQ ID NO: 8)

cctgcaggcagctgcgcgctcgctcgctcactgaggccgcccgggcaaagcccgggcgtcgggcgacctttggtcgcccggcctcagt gagcgagcgagcgcgcagagagggagtggccaactccatcactaggggttcctgcggcctctagaatggaggcggtactatgtagatg agaattcaggagcaaactgggaaaagcaactgcttccaaatatttgtgatttttacagtgtagttttggaaaaactcttagcctaccaattcttct aagtgttttaaaatgtgggagccagtacacatgaagttatagagtgttttaatgaggcttaaatatttaccgtaactatgaaatgctacgcatatc -continued atgctgttcaggctccgtggccacgcaactcatactaccggtgtcgacgccaccatgcttcaactgcctccacttgaaagactgacactgaa
catccccgctctggtggaaaaccagaagaagtactttggcacctacagcgtgatggccatgctgaacgctcagaccgtgctggaccacat
ccagaaggtggccgatattgagggcgagcagaacgagaacaacgagaatctgtggtttcaccccgtgatgagccacctgtacaacgcca
agaacggctacgacaagcagcccgagaaaaccatgttcatcatcgagcggctgcagagctacttcccattcctgaagatcatggccgaga
accagagagagtacagcaacggcaagtacaagcagaaccgcgtggaagtgaacagcaacgacatcttcgaggtgctgaagcgcgcctt
cggcgtgctgaagatgtacagggacctgaccaacgcatacaagacctacgaggaaaagctgaacgacggctgcgagttcctgaccagc
acagagcaacctctgagcggcatgatcaacaactactacacagtggccctgcggaacatgaacgagagatacggctacaagacagagg
acctggccttcatccaggacaagcggttcaagttcgtgaaggacgcctacggcaagaaaaagtcccaagtgaataccggattcttcctgag
cctgcaggactacaacggcgacacacagaagaagctgcacctgagcggagtgggaatcgccctgctgatctgcctgttcctggacaagc
agtacatcaacatctttctgagcaggctgcccatcttctccagctacaatgcccagagcgaggaacggcggatcatcatcagatccttcggc
atcaacagcatcaagctgcccaaggaccggattcacagcgagaagtccaacaagagcgtggccatggatatgctcaacgaagtgaagc
ggtgccccgacgagctgttcacaacactgtctgccgagaagcagtcccggttcagaatcatcagcgacgaccacaatgaagtgctgatga
agcggagcagcgacagattcgtgcctctgctgctgcagtatatcgattacggcaagctgttcgaccacatcaggttccacgtgaacatggg
caagctgagatacctgctgaaggccgacaagacctgcatcgacggccagaccagagtcagagtgatcgagcagcccctgaacggcttc
ggcagactggaagaggccgagacaatgcggaagcaagagaacggcaccttcggcaacagcggcatccggatcagagacttcgagaa
catgaagcgggacgacgccaatcctgccaactatccctacatcgtggacacctacacacactacatcctggaaaacaacaaggtcgagat
gtttatcaacgacaaagaggacagcgccccactgctgcccgtgatcgaggatgatagatacgtggtcaagacaatccccagctgccggat
gagcaccctggaaattccagccatggccttccacatgtttctgttcggcagcaagaaaaccgagaagctgatcgtggacgtgcacaaccg
gtacaagagactgttccaggccatgcagaaagaagaagtgaccgccgagaatatcgccagcttcggaatcgccgagagcgacctgcctc
agaagatcctggatctgatcagcggcaatgcccacggcaaggatgtggacgccttcatcagactgaccgtggacgacatgctgaccgac
accgagcggagaatcaagagattcaaggacgaccggaagtccattcggagcgccgacaacaagatgggaaagagaggcttcaagcag
atctccacaggcaagctggccgacttcctggccaaggacatcgtgctgtttcagcccagcgtgaacgatggcgagaacaagatcaccgg
cctgaactaccggatcatgcagagcgccattgccgtgtacgatagcggcgacgattacgaggccaagcagcagttcaagctgatgttcga
gaaggcccggctgatcggcaagggcacaacagagcctcatccatttctgtacaaggtgttcgcccgcagcatccccgccaatgccgtcga
gttctacgagcgctacctgatcgagcggaagttctacctgaccggcctgtccaacgagatcaagaaaggcaacagagtggatgtgcccttc
atccggcgggaccagaacaagtggaaaacacccgccatgaagaccctgggcagaatctacagcgaggatctgcccgtggaactgccca
gacagatgttcgacaatgagatcaagtcccacctgaagtccctgccacagatggaaggcatcgacttcaacaatgccaacgtgacctatct
gatcgccgagtacatgaagagagtgctggacgacgacttccagaccttctaccagtggaaccgcaactaccggtacatggacatgcttaa
gggcgagtacgacagaaagggctccctgcagcactgcttcaccagcgtggaagagagagaaggcctctggaaagagcgggcctccag
aacagagcggtacagaaagcaggccagcaacaagatccgcagcaaccggcagatgagaaacgccagcagcgaagagatcgagaca
atcctggataagcggctgagcaacagccggaacgagtaccagaaaagcgagaaagtgatccggcgctacagagtgcaggatgccctgc
tgtttctgctggccaaaaagaccctgaccgaactggccgatttcgacggcgagaggttcaaactgaaagaaatcatgcccgacgccgaga
agggaatcctgagcgagatcatgcccatgagcttcaccttcgagaaaggcggcaagaagtacaccatcaccagcgagggcatgaagctg
aagaactacggcgacttctttgtgctggctagcgacaagaggatcggcaacctgctggaactcgtgggcagcgacatcgtgtccaaagag
gatggatcccttcaactgcctccacttgaaagactgacactgtacccatacgatgttccagattacgctggatcccagctgcatttaccgcag
gttttagctgacgctgtctcacgcctggtcctgggtaagtttggtgacctgaccgacaacttctcctcccctcacgctcgcagaaaagtgctg
gctggagtcgtcatgacaacaggcacagatgttaaagatgccaaggtgataagtgtttctacaggaggcaaatgtattaatggtgaatacat
gagtgatcgtggccttgcattaaatgactgccatgcagaaataatatctcggagatccttgctcagatttctttatacacaacttgagctttactta
aataacaaagatgatcaaaaaaagatccatctttcagaaatcagagcgagggggtttaggctgaaggagaatgtccagtttcatctgtacat
cagcacctctccctgtggagatgccagaatcttctcaccacatgagccaatcctggaagaaccagcagatagacacccaaatcgtaaagc -continued aagaggacagctacggaccaaaatagagtctggtcaggggacgattccagtgcgctccaatgcgagcatccaaacgtgggacggggtg ctgcaaggggagcggctgctcaccatgtcctgcagtgacaagattgcacgctggaacgtggtgggcatccagggatcactgctcagcatt ttcgtggagcccatttacttctcgagcatcatcctgggcagcctttaccacggggaccacctttccagggccatgtaccagcggatctccaac atagaggacctgccacctctctacaccctcaacaagcctttgctcagtggcatcagcaatgcagaagcacggcagccagggaaggcccc caacttcagtgtcaactggacggtaggcgactccgctattgaggtcatcaacgccacgactgggaaggatgagctgggccgcgcgtccc gcctgtgtaagcacgcgttgtactgtcgctggatgcgtgtgcacggcaaggttccctcccacttactacgctccaagattaccaagcccaac gtgtaccatgagtccaagctggcggcaaaggagtaccaggccgccaaggcgcgtctgttcacagccttcatcaaggcggggctggggg cctgggtggagaagcccaccgagcaggaccagttctcactcacgtaaaagcttgaattcgatctttttccctctgccaaaaattatggggaca tcatgaagccccttgagcatctgacttctggctaataaaggaaatttattttcattgcaatagtgtgttggaattttttgtgtctctcactcggcggc cgcaggaacccctagtgatggagttggccactccctctctgcgcgctcgctcgctcactgaggccgggcgaccaaaggtcgcccgacgc ccgggctttgcccgggcggcctcagtgagcgagcgagcgcgcagctgcctgcagg > nucleic acid sequence encoding human mutant ADAR2dd with E488Q/T375G mutations (SEQ ID NO: 9)

ATGCAGCTGCATTTACCGCAGGTTTTAGCTGACGCTGTCTCACGCCTGGTCCTGGGT

AAGTTTGGTGACCTGACCGACAACTTCTCCTCCCCTCACGCTCGCAGAAAAGTGCTG

GCTGGAGTCGTCATGACAACAGGCACAGATGTTAAAGATGCCAAGGTGATAAGTGT

TTCTACAGGAGGCAAATGTATTAATGGTGAATACATGAGTGATCGTGGCCTTGCATT

AAATGACTGCCATGCAGAAATAATATCTCGGAGATCCTTGCTCAGATTTCTTTATAC

ACAACTTGAGCTTTACTTAAATAACAAAGATGATCAAAAAAGATCCATCTTTCAGA

AATCAGAGCGAGGGGGGTTTAGGCTGAAGGAGAATGTCCAGTTTCATCTGTACATC

AGCACCTCTCCCTGTGGAGATGCCAGAATCTTCTCACCACATGAGCCAATCCTGGAA

GAACCAGCAGATAGACACCCAAATCGTAAAGCAAGAGGACAGCTACGGACCAAAA

TAGAGTCTGGTCAGGGGACGATTCCAGTGCGCTCCAATGCGAGCATCCAAACGTGG

GACGGGGTGCTGCAAGGGGAGCGGCTGCTCACCATGTCCTGCAGTGACAAGATTGC

ACGCTGGAACGTGGTGGGCATCCAGGGATCACTGCTCAGCATTTTCGTGGAGCCCA

TTTACTTCTCGAGCATCATCCTGGGCAGCCTTTACCACGGGGACCACCTTTCCAGGG

CCATGTACCAGCGGATCTCCAACATAGAGGACCTGCCACCTCTCTACACCCTCAACA

AGCCTTTGCTCAGTGGCATCAGCAATGCAGAAGCACGGCAGCCAGGGAAGGCCCCC

AACTTCAGTGTCAACTGGACGGTAGGCGACTCCGCTATTGAGGTCATCAACGCCAC

GACTGGGAAGGATGAGCTGGGCCGCGCGTCCCGCCTGTGTAAGCACGCGTTGTACT

GTCGCTGGATGCGTGTGCACGGCAAGGTTCCCTCCCACTTACTACGCTCCAAGATTA

CCAAGCCCAACGTGTACCATGAGTCCAAGCTGGCGGCAAAGGAGTACCAGGCCGCC

AAGGCGCGTCTGTTCACAGCCTTCATCAAGGCGGGGCTGGGGGCCTGGGTGGAGAA

GCCCACCGAGCAGGACCAGTTCTCACTCACG

> nucleic acid sequence encoding PspCas13b (SEQ ID NO: 10)

AACATCCCCGCTCTGGTGGAAAACCAGAAGAAGTACTTTGGCACCTACAGCGTGAT

GGCCATGCTGAACGCTCAGACCGTGCTGGACCACATCCAGAAGGTGGCCGATATTG

AGGGCGAGCAGAACGAGAACAACGAGAATCTGTGGTTTCACCCCGTGATGAGCCAC

CTGTACAACGCCAAGAACGGCTACGACAAGCAGCCCGAGAAAACCATGTTCATCAT

CGAGCGGCTGCAGAGCTACTTCCCATTCCTGAAGATCATGGCCGAGAACCAGAGAG

AGTACAGCAACGGCAAGTACAAGCAGAACCGCGTGGAAGTGAACAGCAACGACAT

CTTCGAGGTGCTGAAGCGCGCCTTCGGCGTGCTGAAGATGTACAGGGACCTGACCA

-continued

ACGCATACAAGACCTACGAGGAAAAGCTGAACGACGGCTGCGAGTTCCTGACCAGC

ACAGAGCAACCTCTGAGCGGCATGATCAACAACTACTACACAGTGGCCCTGCGGAA

CATGAACGAGAGATACGGCTACAAGACAGAGGACCTGGCCTTCATCCAGGACAAG

CGGTTCAAGTTCGTGAAGGACGCCTACGGCAAGAAAAAGTCCCAAGTGAATACCGG

ATTCTTCCTGAGCCTGCAGGACTACAACGGCGACACACAGAAGAAGCTGCACCTGA

GCGGAGTGGGAATCGCCCTGCTGATCTGCCTGTTCCTGGACAAGCAGTACATCAAC

ATCTTTCTGAGCAGGCTGCCCATCTTCTCCAGCTACAATGCCCAGAGCGAGGAACG

GCGGATCATCATCAGATCCTTCGGCATCAACAGCATCAAGCTGCCCAAGGACCGGA

TTCACAGCGAGAAGTCCAACAAGAGCGTGGCCATGGATATGCTCAACGAAGTGAAG

CGGTGCCCCGACGAGCTGTTCACAACACTGTCTGCCGAGAAGCAGTCCCGGTTCAG

AATCATCAGCGACGACCACAATGAAGTGCTGATGAAGCGGAGCAGCGACAGATTC

GTGCCTCTGCTGCTGCAGTATATCGATTACGGCAAGCTGTTCGACCACATCAGGTTC

CACGTGAACATGGGCAAGCTGAGATACCTGCTGAAGGCCGACAAGACCTGCATCGA

CGGCCAGACCAGAGTCAGAGTGATCGAGCAGCCCCTGAACGGCTTCGGCAGACTGG

AAGAGGCCGAGACAATGCGGAAGCAAGAGAACGGCACCTTCGGCAACAGCGGCAT

CCGGATCAGAGACTTCGAGAACATGAAGCGGGACGACGCCAATCCTGCCAACTATC

CCTACATCGTGGACACCTACACACACTACATCCTGGAAAACAACAAGGTCGAGATG

TTTATCAACGACAAAGAGGACAGCGCCCCACTGCTGCCCGTGATCGAGGATGATAG

ATACGTGGTCAAGACAATCCCCAGCTGCCGGATGAGCACCCTGGAAATTCCAGCCA

TGGCCTTCCACATGTTTCTGTTCGGCAGCAAGAAAACCGAGAAGCTGATCGTGGAC

GTGCACAACCGGTACAAGAGACTGTTCCAGGCCATGCAGAAAGAAGAAGTGACCG

CCGAGAATATCGCCAGCTTCGGAATCGCCGAGAGCGACCTGCCTCAGAAGATCCTG

GATCTGATCAGCGGCAATGCCCACGGCAAGGATGTGGACGCCTTCATCAGACTGAC

CGTGGACGACATGCTGACCGACACCGAGCGGAGAATCAAGAGATTCAAGGACGAC

CGGAAGTCCATTCGGAGCGCCGACAACAAGATGGGAAAGAGAGGCTTCAAGCAGA

TCTCCACAGGCAAGCTGGCCGACTTCCTGGCCAAGGACATCGTGCTGTTTCAGCCCA

GCGTGAACGATGGCGAGAACAAGATCACCGGCCTGAACTACCGGATCATGCAGAG

CGCCATTGCCGTGTACGATAGCGGCGACGATTACGAGGCCAAGCAGCAGTTCAAGC

TGATGTTCGAGAAGGCCCGGCTGATCGGCAAGGGCACAACAGAGCCTCATCCATTT

CTGTACAAGGTGTTCGCCCGCAGCATCCCCGCCAATGCCGTCGAGTTCTACGAGCGC

TACCTGATCGAGCGGAAGTTCTACCTGACCGGCCTGTCCAACGAGATCAAGAAAGG

CAACAGAGTGGATGTGCCCTTCATCCGGCGGGACCAGAACAAGTGGAAAACACCCG

CCATGAAGACCCTGGGCAGAATCTACAGCGAGGATCTGCCCGTGGAACTGCCCAGA

CAGATGTTCGACAATGAGATCAAGTCCCACCTGAAGTCCCTGCCACAGATGGAAGG

CATCGACTTCAACAATGCCAACGTGACCTATCTGATCGCCGAGTACATGAAGAGAG

TGCTGGACGACGACTTCCAGACCTTCTACCAGTGGAACCGCAACTACCGGTACATG

GACATGCTTAAGGGCGAGTACGACAGAAAGGGCTCCCTGCAGCACTGCTTCACCAG

CGTGGAAGAGAGAGAAGGCCTCTGGAAAGAGCGGGCCTCCAGAACAGAGCGGTAC

AGAAAGCAGGCCAGCAACAAGATCCGCAGCAACCGGCAGATGAGAAACGCCAGCA

GCGAAGAGATCGAGACAATCCTGGATAAGCGGCTGAGCAACAGCCGGAACGAGTA

-continued

CCAGAAAAGCGAGAAAGTGATCCGGCGCTACAGAGTGCAGGATGCCCTGCTGTTTC

TGCTGGCCAAAAAGACCCTGACCGAACTGGCCGATTTCGACGGCGAGAGGTTCAAA

CTGAAAGAAATCATGCCCGACGCCGAGAAGGGAATCCTGAGCGAGATCATGCCCAT

GAGCTTCACCTTCGAGAAAGGCGGCAAGAAGTACACCATCACCAGCGAGGGCATG

AAGCTGAAGAACTACGGCGACTTCTTTGTGCTGGCTAGCGACAAGAGGATCGGCAA

CCTGCTGGAACTCGTGGGCAGCGACATCGTGTCCAAAGAGGAT

What is claimed is:

1. An isolated nucleic acid comprising an expression cassette encoding:

(i) a first region comprising a catalytically inactive Cas13b protein;

(ii) a second region comprising a first signal sequence;

(iii) a third region comprising an Adenosine Deaminase Acting on RNA deaminase domain (ADARdd); and (iv) a fourth region comprising a second signal sequence, wherein the expression cassette is flanked by adeno-associated virus (AAV) inverted terminal repeats (ITRs), and the size of the construct is less than 5 kb;

wherein the first signal sequence or the second signal sequence is a nuclear localization signal (NLS) comprising the nucleic acid sequence set forth in SEQ ID NO: 4.

2. The isolated nucleic acid of claim 1, wherein the catalytically inactive Cas13b is a dCas13b protein comprises the amino acid sequence set forth in SEQ ID NO: 1 or is encoded by the nucleic acid sequence set forth in SEQ ID NO: 10.

3. The isolated nucleic acid of claim 1, wherein the ADARdd comprises the amino acid sequence set forth in SEQ ID NO: 2 or is encoded by the nucleic acid sequence set forth in SEQ ID NO: 9.

4. The isolated nucleic acid of claim 1, further comprising one or more linking polynucleotides, wherein each linking polynucleotide encodes a glycine-serine (GS) linker.

5. The isolated nucleic acid of claim 1, further comprising a promoter, wherein the promoter is a Ula promoter, H1 promoter, or a small synthetic promoter.

6. The isolated nucleic acid of claim 5, wherein the promoter is operably linked to the second region or wherein the promoter is operably linked to the third region.

7. The isolated nucleic acid of claim 1 further comprising a poly-adenylation (polyA) signal, wherein the polyA signal is a rabbit beta-globulin polyA (RGB polyA).

8. The isolated nucleic acid of claim 1, comprising the sequence set forth in SEQ ID NO: 5 or 6.

9. A recombinant adeno-associated virus (rAAV) comprising:

(i) the isolated nucleic acid of claim 1; and (ii) an AAV capsid protein.

10. The rAAV of claim 9, wherein the capsid protein is an AAV1, AAV2, AAV3, AAV4, AAV5, AAV6, AAV7, AAV8, AAV9 capsid protein, or a variant thereof.

11. A pharmaceutical composition comprising the isolated nucleic acid of claim 1, and a pharmaceutically acceptable excipient.

* * * * *

SEQUENCE LISTING

<160> NUMBER OF SEQ ID NOS: 17

<210> SEQ ID NO 1
<211> LENGTH: 982
<212> TYPE: PRT
<213> ORGANISM: Artificial Sequence
<220> FEATURE:
<223> OTHER INFORMATION: Synthetic

<400> SEQUENCE: 1

Asn Ile Pro Ala Leu Val Glu Asn Gln Lys Lys Tyr Phe Gly Thr Tyr
1               5                   10                  15

Ser Val Met Ala Met Leu Asn Ala Gln Thr Val Leu Asp His Ile Gln
            20                  25                  30

Lys Val Ala Asp Ile Glu Gly Glu Gln Asn Glu Asn Asn Glu Asn Leu
        35                  40                  45

Trp Phe His Pro Val Met Ser His Leu Tyr Asn Ala Lys Asn Gly Tyr
    50                  55                  60

Asp Lys Gln Pro Glu Lys Thr Met Phe Ile Ile Glu Arg Leu Gln Ser
65                  70                  75                  80

Tyr Phe Pro Phe Leu Lys Ile Met Ala Glu Asn Gln Arg Glu Tyr Ser
                85                  90                  95

Asn Gly Lys Tyr Lys Gln Asn Arg Val Glu Val Asn Ser Asn Asp Ile
            100                 105                 110

Phe Glu Val Leu Lys Arg Ala Phe Gly Val Leu Lys Met Tyr Arg Asp
        115                 120                 125

Leu Thr Asn Ala Tyr Lys Thr Tyr Glu Glu Lys Leu Asn Asp Gly Cys
    130                 135                 140

Glu Phe Leu Thr Ser Thr Glu Gln Pro Leu Ser Gly Met Ile Asn Asn
145                 150                 155                 160

Tyr Tyr Thr Val Ala Leu Arg Asn Met Asn Glu Arg Tyr Gly Tyr Lys
                165                 170                 175

Thr Glu Asp Leu Ala Phe Ile Gln Asp Lys Arg Phe Lys Phe Val Lys
            180                 185                 190

Asp Ala Tyr Gly Lys Lys Lys Ser Gln Val Asn Thr Gly Phe Phe Leu
        195                 200                 205

Ser Leu Gln Asp Tyr Asn Gly Asp Thr Gln Lys Lys Leu His Leu Ser
    210                 215                 220

Gly Val Gly Ile Ala Leu Leu Ile Cys Leu Phe Leu Asp Lys Gln Tyr
225                 230                 235                 240

Ile Asn Ile Phe Leu Ser Arg Leu Pro Ile Phe Ser Ser Tyr Asn Ala
                245                 250                 255

Gln Ser Glu Glu Arg Arg Ile Ile Ile Arg Ser Phe Gly Ile Asn Ser
            260                 265                 270

Ile Lys Leu Pro Lys Asp Arg Ile His Ser Glu Lys Ser Asn Lys Ser

```
        275                 280                 285

Val Ala Met Asp Met Leu Asn Glu Val Lys Arg Cys Pro Asp Glu Leu
    290                 295                 300

Phe Thr Thr Leu Ser Ala Glu Lys Gln Ser Arg Phe Arg Ile Ile Ser
305                 310                 315                 320

Asp Asp His Asn Glu Val Leu Met Lys Arg Ser Ser Asp Arg Phe Val
                325                 330                 335

Pro Leu Leu Leu Gln Tyr Ile Asp Tyr Gly Lys Leu Phe Asp His Ile
            340                 345                 350

Arg Phe His Val Asn Met Gly Lys Leu Arg Tyr Leu Leu Lys Ala Asp
        355                 360                 365

Lys Thr Cys Ile Asp Gly Gln Thr Arg Val Arg Val Ile Glu Gln Pro
    370                 375                 380

Leu Asn Gly Phe Gly Arg Leu Glu Glu Ala Glu Thr Met Arg Lys Gln
385                 390                 395                 400

Glu Asn Gly Thr Phe Gly Asn Ser Gly Ile Arg Ile Arg Asp Phe Glu
                405                 410                 415

Asn Met Lys Arg Asp Asp Ala Asn Pro Ala Asn Tyr Pro Tyr Ile Val
            420                 425                 430

Asp Thr Tyr Thr His Tyr Ile Leu Glu Asn Asn Lys Val Glu Met Phe
        435                 440                 445

Ile Asn Asp Lys Glu Asp Ser Ala Pro Leu Leu Pro Val Ile Glu Asp
    450                 455                 460

Asp Arg Tyr Val Val Lys Thr Ile Pro Ser Cys Arg Met Ser Thr Leu
465                 470                 475                 480

Glu Ile Pro Ala Met Ala Phe His Met Phe Leu Phe Gly Ser Lys Lys
                485                 490                 495

Thr Glu Lys Leu Ile Val Asp Val His Asn Arg Tyr Lys Arg Leu Phe
            500                 505                 510

Gln Ala Met Gln Lys Glu Glu Val Thr Ala Glu Asn Ile Ala Ser Phe
        515                 520                 525

Gly Ile Ala Glu Ser Asp Leu Pro Gln Lys Ile Leu Asp Leu Ile Ser
    530                 535                 540

Gly Asn Ala His Gly Lys Asp Val Asp Ala Phe Ile Arg Leu Thr Val
545                 550                 555                 560

Asp Asp Met Leu Thr Asp Thr Glu Arg Arg Ile Lys Arg Phe Lys Asp
                565                 570                 575

Asp Arg Lys Ser Ile Arg Ser Ala Asp Asn Lys Met Gly Lys Arg Gly
            580                 585                 590

Phe Lys Gln Ile Ser Thr Gly Lys Leu Ala Asp Phe Leu Ala Lys Asp
        595                 600                 605

Ile Val Leu Phe Gln Pro Ser Val Asn Asp Gly Glu Asn Lys Ile Thr
    610                 615                 620

Gly Leu Asn Tyr Arg Ile Met Gln Ser Ala Ile Ala Val Tyr Asp Ser
625                 630                 635                 640

Gly Asp Asp Tyr Glu Ala Lys Gln Gln Phe Lys Leu Met Phe Glu Lys
                645                 650                 655

Ala Arg Leu Ile Gly Lys Gly Thr Thr Glu Pro His Pro Phe Leu Tyr
            660                 665                 670

Lys Val Phe Ala Arg Ser Ile Pro Ala Asn Ala Val Glu Phe Tyr Glu
        675                 680                 685

Arg Tyr Leu Ile Glu Arg Lys Phe Tyr Leu Thr Gly Leu Ser Asn Glu
    690                 695                 700
```

Ile Lys Lys Gly Asn Arg Val Asp Val Pro Phe Ile Arg Arg Asp Gln
705 710 715 720

Asn Lys Trp Lys Thr Pro Ala Met Lys Thr Leu Gly Arg Ile Tyr Ser
725 730 735

Glu Asp Leu Pro Val Glu Leu Pro Arg Gln Met Phe Asp Asn Glu Ile
740 745 750

Lys Ser His Leu Lys Ser Leu Pro Gln Met Glu Gly Ile Asp Phe Asn
755 760 765

Asn Ala Asn Val Thr Tyr Leu Ile Ala Glu Tyr Met Lys Arg Val Leu
770 775 780

Asp Asp Asp Phe Gln Thr Phe Tyr Gln Trp Asn Arg Asn Tyr Arg Tyr
785 790 795 800

Met Asp Met Leu Lys Gly Glu Tyr Asp Arg Lys Gly Ser Leu Gln His
805 810 815

Cys Phe Thr Ser Val Glu Glu Arg Glu Gly Leu Trp Lys Glu Arg Ala
820 825 830

Ser Arg Thr Glu Arg Tyr Arg Lys Gln Ala Ser Asn Lys Ile Arg Ser
835 840 845

Asn Arg Gln Met Arg Asn Ala Ser Ser Glu Glu Ile Glu Thr Ile Leu
850 855 860

Asp Lys Arg Leu Ser Asn Ser Arg Asn Glu Tyr Gln Lys Ser Glu Lys
865 870 875 880

Val Ile Arg Arg Tyr Arg Val Gln Asp Ala Leu Leu Phe Leu Leu Ala
885 890 895

Lys Lys Thr Leu Thr Glu Leu Ala Asp Phe Asp Gly Glu Arg Phe Lys
900 905 910

Leu Lys Glu Ile Met Pro Asp Ala Glu Lys Gly Ile Leu Ser Glu Ile
915 920 925

Met Pro Met Ser Phe Thr Phe Glu Lys Gly Gly Lys Lys Tyr Thr Ile
930 935 940

Thr Ser Glu Gly Met Lys Leu Lys Asn Tyr Gly Asp Phe Phe Val Leu
945 950 955 960

Ala Ser Asp Lys Arg Ile Gly Asn Leu Leu Glu Leu Val Gly Ser Asp
965 970 975

Ile Val Ser Lys Glu Asp
980

<210> SEQ ID NO 2
<211> LENGTH: 385
<212> TYPE: PRT
<213> ORGANISM: Artificial Sequence
<220> FEATURE:
<223> OTHER INFORMATION: Synthetic

<400> SEQUENCE: 2

Gln Leu His Leu Pro Gln Val Leu Ala Asp Ala Val Ser Arg Leu Val
1 5 10 15

Leu Gly Lys Phe Gly Asp Leu Thr Asp Asn Phe Ser Ser Pro His Ala
20 25 30

Arg Arg Lys Val Leu Ala Gly Val Val Met Thr Thr Gly Thr Asp Val
35 40 45

Lys Asp Ala Lys Val Ile Ser Val Ser Thr Gly Gly Lys Cys Ile Asn
50 55 60

Gly Glu Tyr Met Ser Asp Arg Gly Leu Ala Leu Asn Asp Cys His Ala
65 70 75 80

```
Glu Ile Ile Ser Arg Arg Ser Leu Leu Arg Phe Leu Tyr Thr Gln Leu
                85                  90                  95

Glu Leu Tyr Leu Asn Asn Lys Asp Asp Gln Lys Arg Ser Ile Phe Gln
            100                 105                 110

Lys Ser Glu Arg Gly Gly Phe Arg Leu Lys Glu Asn Val Gln Phe His
        115                 120                 125

Leu Tyr Ile Ser Thr Ser Pro Cys Gly Asp Ala Arg Ile Phe Ser Pro
    130                 135                 140

His Glu Pro Ile Leu Glu Glu Pro Ala Asp Arg His Pro Asn Arg Lys
145                 150                 155                 160

Ala Arg Gly Gln Leu Arg Thr Lys Ile Glu Ser Gly Gln Gly Thr Ile
                165                 170                 175

Pro Val Arg Ser Asn Ala Ser Ile Gln Thr Trp Asp Gly Val Leu Gln
            180                 185                 190

Gly Glu Arg Leu Leu Thr Met Ser Cys Ser Asp Lys Ile Ala Arg Trp
        195                 200                 205

Asn Val Val Gly Ile Gln Gly Ser Leu Leu Ser Ile Phe Val Glu Pro
    210                 215                 220

Ile Tyr Phe Ser Ser Ile Ile Leu Gly Ser Leu Tyr His Gly Asp His
225                 230                 235                 240

Leu Ser Arg Ala Met Tyr Gln Arg Ile Ser Asn Ile Glu Asp Leu Pro
                245                 250                 255

Pro Leu Tyr Thr Leu Asn Lys Pro Leu Leu Ser Gly Ile Ser Asn Ala
            260                 265                 270

Glu Ala Arg Gln Pro Gly Lys Ala Pro Asn Phe Ser Val Asn Trp Thr
        275                 280                 285

Val Gly Asp Ser Ala Ile Glu Val Ile Asn Ala Thr Thr Gly Lys Asp
    290                 295                 300

Glu Leu Gly Arg Ala Ser Arg Leu Cys Lys His Ala Leu Tyr Cys Arg
305                 310                 315                 320

Trp Met Arg Val His Gly Lys Val Pro Ser His Leu Leu Arg Ser Lys
                325                 330                 335

Ile Thr Lys Pro Asn Val Tyr His Glu Ser Lys Leu Ala Ala Lys Glu
            340                 345                 350

Tyr Gln Ala Ala Lys Ala Arg Leu Phe Thr Ala Phe Ile Lys Ala Gly
        355                 360                 365

Leu Gly Ala Trp Val Glu Lys Pro Thr Glu Gln Asp Gln Phe Ser Leu
    370                 375                 380

Thr
385
```

<210> SEQ ID NO 3
<211> LENGTH: 33
<212> TYPE: DNA
<213> ORGANISM: Artificial Sequence
<220> FEATURE:
<223> OTHER INFORMATION: Synthetic

<400> SEQUENCE: 3
cttcaactgc ctccacttga aagactgaca ctg 33

<210> SEQ ID NO 4
<211> LENGTH: 27
<212> TYPE: DNA
<213> ORGANISM: Artificial Sequence
<220> FEATURE:

<223> OTHER INFORMATION: Synthetic

<400> SEQUENCE: 4
cctgcagcta agcgggttaa gttggat 27

<210> SEQ ID NO 5
<211> LENGTH: 4922
<212> TYPE: DNA
<213> ORGANISM: Artificial Sequence
<220> FEATURE:
<223> OTHER INFORMATION: Synthetic

<400> SEQUENCE: 5
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggcctct agaatggagg cggtactatg tagatgagaa 180
ttcaggagca aactgggaaa agcaactgct tccaaatatt tgtgattttt acagtgtagt 240
tttggaaaaa ctcttagcct accaattctt ctaagtgttt taaaatgtgg gagccagtac 300
acatgaagtt atagagtgtt ttaatgaggc ttaaatattt accgtaacta tgaaatgcta 360
cgcatatcat gctgttcagg ctccgtggcc acgcaactca tactaccggt gtcgacgcca 420
ccatgcagct gcatttaccg caggttttag ctgacgctgt ctcacgcctg gtcctgggta 480
agtttggtga cctgaccgac aacttctcct cccctcacgc tcgcagaaaa gtgctggctg 540
gagtcgtcat gacaacaggc acagatgtta aagatgccaa ggtgataagt gtttctacag 600
gaggcaaatg tattaatggt gaatacatga gtgatcgtgg ccttgcatta aatgactgcc 660
atgcagaaat aatatctcgg agatccttgc tcagatttct ttatacacaa cttgagcttt 720
acttaaataa caaagatgat caaaaaagat ccatctttca gaaatcagag cgagggggt 780 ttaggctgaa ggagaatgtc cagtttcatc tgtacatcag cacctctccc tgtggagatg 840
ccagaatctt ctcaccacat gagccaatcc tggaagaacc agcagataga cacccaaatc 900
gtaaagcaag aggacagcta cggaccaaaa tagagtctgg tcaggggacg attccagtgc 960
gctccaatgc gagcatccaa acgtgggacg gggtgctgca aggggagcgg ctgctcacca 1020
tgtcctgcag tgacaagatt gcacgctgga acgtggtggg catccaggga tcactgctca 1080
gcattttcgt ggagcccatt tacttctcga gcatcatcct gggcagcctt taccacgggg 1140
accacctttc cagggccatg taccagcgga tctccaacat agaggacctg ccacctctct 1200
acaccctcaa caagcctttg ctcagtggca tcagcaatgc agaagcacgg cagccaggga 1260
aggcccccaa cttcagtgtc aactggacgg taggcgactc cgctattgag gtcatcaacg 1320
ccacgactgg gaaggatgag ctgggccgcg cgtcccgcct gtgtaagcac gcgttgtact 1380
gtcgctggat gcgtgtgcac ggcaaggttc cctcccactt actacgctcc aagattacca 1440
agcccaacgt gtaccatgag tccaagctgg cggcaaagga gtaccaggcc gccaaggcgc 1500
gtctgttcac agccttcatc aaggcggggc tgggggcctg ggtggagaag cccaccgagc 1560
aggaccagtt ctcactcacg ggatcccctg cagctaagcg ggttaagttg gatggatcca 1620
acatccccgc tctggtggaa aaccagaaga agtactttgg cacctacagc gtgatggcca 1680
tgctgaacgc tcagaccgtg ctggaccaca tccagaaggt ggccgatatt gagggcgagc 1740
agaacgagaa caacgagaat ctgtggtttc accccgtgat gagccacctg tacaacgcca 1800
agaacggcta cgacaagcag cccgagaaaa ccatgttcat catcgagcgg ctgcagagct 1860
acttcccatt cctgaagatc atggccgaga accagagaga gtacagcaac ggcaagtaca 1920

```
agcagaaccg cgtggaagtg aacagcaacg acatcttcga ggtgctgaag cgcgccttcg   1980
gcgtgctgaa gatgtacagg gacctgacca acgcatacaa gacctacgag gaaaagctga   2040
acgacggctg cgagttcctg accagcacag agcaacctct gagcggcatg atcaacaact   2100
actacacagt ggccctgcgg aacatgaacg agagatacgg ctacaagaca gaggacctgg   2160
ccttcatcca ggacaagcgg ttcaagttcg tgaaggacgc ctacggcaag aaaaagtccc   2220
aagtgaatac cggattcttc ctgagcctgc aggactacaa cggcgacaca cagaagaagc   2280
tgcacctgag cggagtggga atcgccctgc tgatctgcct gttcctggac aagcagtaca   2340
tcaacatctt tctgagcagg ctgcccatct tctccagcta caatgcccag agcgaggaac   2400
ggcggatcat catcagatcc ttcggcatca acagcatcaa gctgcccaag gaccggattc   2460
acagcgagaa gtccaacaag agcgtggcca tggatatgct caacgaagtg aagcggtgcc   2520
ccgacgagct gttcacaaca ctgtctgccg agaagcagtc ccggttcaga atcatcagcg   2580
acgaccacaa tgaagtgctg atgaagcgga gcagcgacag attcgtgcct ctgctgctgc   2640
agtatatcga ttacggcaag ctgttcgacc acatcaggtt ccacgtgaac atgggcaagc   2700
tgagatacct gctgaaggcc gacaagacct gcatcgacgg ccagaccaga gtcagagtga   2760
tcgagcagcc cctgaacggc ttcggcagac tggaagaggc cgagacaatg cggaagcaag   2820
agaacggcac cttcggcaac agcggcatcc ggatcagaga cttcgagaac atgaagcggg   2880
acgacgccaa tcctgccaac tatccctaca tcgtggacac ctacacacac tacatcctgg   2940
aaaacaacaa ggtcgagatg tttatcaacg acaaagagga cagcgcccca ctgctgcccg   3000
tgatcgagga tgatagatac gtggtcaaga caatccccag ctgccggatg agcaccctgg   3060
aaattccagc catggccttc cacatgtttc tgttcggcag caagaaaacc gagaagctga   3120
tcgtggacgt gcacaaccgg tacaagagac tgttccaggc catgcagaaa gaagaagtga   3180
ccgccgagaa tatcgccagc ttcggaatcg ccgagagcga cctgcctcag aagatcctgg   3240
atctgatcag cggcaatgcc cacggcaagg atgtggacgc cttcatcaga ctgaccgtgg   3300
acgacatgct gaccgacacc gagcggagaa tcaagagatt caaggacgac cggaagtcca   3360
ttcggagcgc cgacaacaag atgggaaaga gaggcttcaa gcagatctcc acaggcaagc   3420
tggccgactt cctggccaag gacatcgtgc tgtttcagcc cagcgtgaac gatggcgaga   3480
acaagatcac cggcctgaac taccggatca tgcagagcgc cattgccgtg tacgatagcg   3540
gcgacgatta cgaggccaag cagcagttca agctgatgtt cgagaaggcc cggctgatcg   3600
gcaagggcac aacagagcct catccatttc tgtacaaggt gttcgcccgc agcatccccg   3660
ccaatgccgt cgagttctac gagcgctacc tgatcgagcg gaagttctac ctgaccggcc   3720
tgtccaacga gatcaagaaa ggcaacagag tggatgtgcc cttcatccgg cgggaccaga   3780
acaagtggaa aacacccgcc atgaagaccc tgggcagaat ctacagcgag gatctgcccg   3840
tggaactgcc cagacagatg ttcgacaatg agatcaagtc ccacctgaag tccctgccac   3900
agatggaagg catcgacttc aacaatgcca acgtgaccta tctgatcgcc gagtacatga   3960
agagagtgct ggacgacgac ttccagacct tctaccagtg gaaccgcaac taccggtaca   4020
tggacatgct taagggcgag tacgacagaa agggctccct gcagcactgc ttcaccagcg   4080
tggaagagag agaaggcctc tggaaagagc gggcctccag aacagagcgg tacagaaagc   4140
aggccagcaa caagatccgc agcaaccggc agatgagaaa cgccagcagc gaagagatcg   4200
agacaatcct ggataagcgg ctgagcaaca gccggaacga gtaccagaaa agcgagaaag   4260
```

tgatccggcg ctacagagtg caggatgccc tgctgtttct gctggccaaa aagaccctga 4320
ccgaactggc cgatttcgac ggcgagaggt tcaaactgaa agaaatcatg cccgacgccg 4380
agaagggaat cctgagcgag atcatgccca tgagcttcac cttcgagaaa ggcggcaaga 4440
agtacaccat caccagcgag ggcatgaagc tgaagaacta cggcgacttc tttgtgctgg 4500
ctagcgacaa gaggatcggc aacctgctgg aactcgtggg cagcgacatc gtgtccaaag 4560
aggatggatc ccctgcagct aagcgggtta agttggatgg atcctaccca tacgatgttc 4620
cagattacgc ttaaaagctt gaattcgatc tttttccctc tgccaaaaat tatggggaca 4680
tcatgaagcc ccttgagcat ctgacttctg gctaataaag gaaatttatt ttcattgcaa 4740
tagtgtgttg gaattttttg tgtctctcac tcggcggccg caggaacccc tagtgatgga 4800
gttggccact ccctctctgc gcgctcgctc gctcactgag gccgggcgac caaaggtcgc 4860
ccgacgcccg ggctttgccc gggcggcctc agtgagcgag cgagcgcgca gctgcctgca 4920
gg 4922

<210> SEQ ID NO 6
<211> LENGTH: 4916
<212> TYPE: DNA
<213> ORGANISM: Artificial Sequence
<220> FEATURE:
<223> OTHER INFORMATION: Synthetic

<400> SEQUENCE: 6
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggcctct agaatggagg cggtactatg tagatgagaa 180
ttcaggagca aactgggaaa agcaactgct tccaaatatt tgtgattttt acagtgtagt 240
tttggaaaaa ctcttagcct accaattctt ctaagtgttt taaaatgtgg gagccagtac 300
acatgaagtt atagagtgtt ttaatgaggc ttaaatattt accgtaacta tgaaatgcta 360
cgcatatcat gctgttcagg ctccgtggcc acgcaactca tactaccggt gtcgacgcca 420
ccatgcctgc agctaagcgg gttaagttgg ataacatccc cgctctggtg gaaaaccaga 480
agaagtactt tggcacctac agcgtgatgg ccatgctgaa cgctcagacc gtgctggacc 540
acatccagaa ggtggccgat attgagggcg agcagaacga gaacaacgag aatctgtggt 600
ttcaccccgt gatgagccac ctgtacaacg ccaagaacgg ctacgacaag cagcccgaga 660
aaaccatgtt catcatcgag cggctgcaga gctacttccc attcctgaag atcatggccg 720
agaaccagag agagtacagc aacggcaagt acaagcagaa ccgcgtggaa gtgaacagca 780
acgacatctt cgaggtgctg aagcgcgcct tcggcgtgct gaagatgtac agggacctga 840
ccaacgcata caagacctac gaggaaaagc tgaacgacgg ctgcgagttc ctgaccagca 900
cagagcaacc tctgagcggc atgatcaaca actactacac agtggccctg cggaacatga 960
acgagagata cggctacaag acagaggacc tggccttcat ccaggacaag cggttcaagt 1020
tcgtgaagga cgcctacggc aagaaaaagt cccaagtgaa taccggattc ttcctgagcc 1080
tgcaggacta caacggcgac acacagaaga agctgcacct gagcggagtg ggaatcgccc 1140
tgctgatctg cctgttcctg gacaagcagt acatcaacat ctttctgagc aggctgccca 1200
tcttctccag ctacaatgcc cagagcgagg aacggcggat catcatcaga tccttcggca 1260
tcaacagcat caagctgccc aaggaccgga ttcacagcga gaagtccaac aagagcgtgg 1320
ccatggatat gctcaacgaa gtgaagcggt gccccgacga gctgttcaca acactgtctg 1380
ccgagaagca gtcccggttc agaatcatca gcgacgacca caatgaagtg ctgatgaagc 1440
ggagcagcga cagattcgtg cctctgctgc tgcagtatat cgattacggc aagctgttcg 1500
accacatcag gttccacgtg aacatgggca agctgagata cctgctgaag gccgacaaga 1560
cctgcatcga cggccagacc agagtcagag tgatcgagca gcccctgaac ggcttcggca 1620
gactggaaga ggccgagaca atgcggaagc aagagaacgg caccttcggc aacagcggca 1680
tccggatcag agacttcgag aacatgaagc gggacgacgc caatcctgcc aactatccct 1740
acatcgtgga cacctacaca cactacatcc tggaaaacaa caaggtcgag atgtttatca 1800
acgacaaaga ggacagcgcc ccactgctgc ccgtgatcga ggatgataga tacgtggtca 1860
agacaatccc cagctgccgg atgagcaccc tggaaattcc agccatggcc ttccacatgt 1920
ttctgttcgg cagcaagaaa accgagaagc tgatcgtgga cgtgcacaac cggtacaaga 1980
gactgttcca ggccatgcag aaagaagaag tgaccgccga gaatatcgcc agcttcggaa 2040
tcgccgagag cgacctgcct cagaagatcc tggatctgat cagcggcaat gcccacggca 2100
aggatgtgga cgccttcatc agactgaccg tggacgacat gctgaccgac accgagcgga 2160
gaatcaagag attcaaggac gaccggaagt ccattcggag cgccgacaac aagatgggaa 2220
agagaggctt caagcagatc tccacaggca agctggccga cttcctggcc aaggacatcg 2280
tgctgtttca gcccagcgtg aacgatggcg agaacaagat caccggcctg aactaccgga 2340
tcatgcagag cgccattgcc gtgtacgata gcggcgacga ttacgaggcc aagcagcagt 2400
tcaagctgat gttcgagaag gcccggctga tcggcaaggg cacaacagag cctcatccat 2460
ttctgtacaa ggtgttcgcc cgcagcatcc ccgccaatgc cgtcgagttc tacgagcgct 2520
acctgatcga gcggaagttc tacctgaccg gcctgtccaa cgagatcaag aaaggcaaca 2580
gagtggatgt gcccttcatc cggcgggacc agaacaagtg gaaaacaccc gccatgaaga 2640
ccctgggcag aatctacagc gaggatctgc ccgtggaact gcccagacag atgttcgaca 2700
atgagatcaa gtcccacctg aagtccctgc cacagatgga aggcatcgac ttcaacaatg 2760
ccaacgtgac ctatctgatc gccgagtaca tgaagagagt gctggacgac gacttccaga 2820
ccttctacca gtggaaccgc aactaccggt acatggacat gcttaagggc gagtacgaca 2880
gaaagggctc cctgcagcac tgcttcacca gcgtggaaga gagagaaggc ctctggaaag 2940
agcgggcctc cagaacagag cggtacagaa agcaggccag caacaagatc cgcagcaacc 3000
ggcagatgag aaacgccagc agcgaagaga tcgagacaat cctggataag cggctgagca 3060
acagccggaa cgagtaccag aaaagcgaga aagtgatccg gcgctacaga gtgcaggatg 3120
ccctgctgtt tctgctggcc aaaaagaccc tgaccgaact ggccgatttc gacggcgaga 3180
ggttcaaact gaaagaaatc atgcccgacg ccgagaaggg aatcctgagc gagatcatgc 3240
ccatgagctt caccttcgag aaaggcggca agaagtacac catcaccagc gagggcatga 3300
agctgaagaa ctacggcgac ttctttgtgc tggctagcga caagaggatc ggcaacctgc 3360
tggaactcgt gggcagcgac atcgtgtcca aagaggatgg atcccctgca gctaagcggg 3420
ttaagttgga tggatcctac ccatacgatg ttccagatta cgctggatcc cagctgcatt 3480
taccgcaggt tttagctgac gctgtctcac gcctggtcct gggtaagttt ggtgacctga 3540
ccgacaactt ctcctcccct cacgctcgca gaaaagtgct ggctggagtc gtcatgacaa 3600
caggcacaga tgttaaagat gccaaggtga taagtgtttc tacaggaggc aaatgtatta 3660
atggtgaata catgagtgat cgtggccttg cattaaatga ctgccatgca gaaataatat 3720
ctcggagatc cttgctcaga tttctttata cacaacttga gctttactta aataacaaag 3780
atgatcaaaa aagatccatc tttcagaaat cagagcgagg ggggtttagg ctgaaggaga 3840
atgtccagtt tcatctgtac atcagcacct ctccctgtgg agatgccaga atcttctcac 3900
cacatgagcc aatcctggaa gaaccagcag atagacaccc aaatcgtaaa gcaagaggac 3960
agctacggac caaaatagag tctggtcagg ggacgattcc agtgcgctcc aatgcgagca 4020
tccaaacgtg ggacggggtg ctgcaagggg agcggctgct caccatgtcc tgcagtgaca 4080
agattgcacg ctggaacgtg gtgggcatcc agggatcact gctcagcatt ttcgtggagc 4140
ccatttactt ctcgagcatc atcctgggca gcctttacca cggggaccac ctttccaggg 4200
ccatgtacca gcggatctcc aacatagagg acctgccacc tctctacacc ctcaacaagc 4260
ctttgctcag tggcatcagc aatgcagaag cacggcagcc agggaaggcc cccaacttca 4320
gtgtcaactg gacggtaggc gactccgcta ttgaggtcat caacgccacg actgggaagg 4380
atgagctggg ccgcgcgtcc cgcctgtgta agcacgcgtt gtactgtcgc tggatgcgtg 4440
tgcacggcaa ggttccctcc cacttactac gctccaagat taccaagccc aacgtgtacc 4500
atgagtccaa gctggcggca aaggagtacc aggccgccaa ggcgcgtctg ttcacagcct 4560
tcatcaaggc ggggctgggg gcctgggtgg agaagcccac cgagcaggac cagttctcac 4620
tcacgtaaaa gcttgaattc gatctttttc cctctgccaa aaattatggg gacatcatga 4680
agccccttga gcatctgact tctggctaat aaaggaaatt tattttcatt gcaatagtgt 4740
gttggaattt tttgtgtctc tcactcggcg gccgcaggaa cccctagtga tggagttggc 4800
cactccctct ctgcgcgctc gctcgctcac tgaggccggg cgaccaaagg tcgcccgacg 4860
cccgggcttt gcccgggcgg cctcagtgag cgagcgagcg cgcagctgcc tgcagg 4916

<210> SEQ ID NO 7
<211> LENGTH: 4922
<212> TYPE: DNA
<213> ORGANISM: Artificial Sequence
<220> FEATURE:
<223> OTHER INFORMATION: Synthetic

<400> SEQUENCE: 7
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggcctct agaatggagg cggtactatg tagatgagaa 180
ttcaggagca aactgggaaa agcaactgct tccaaatatt tgtgattttt acagtgtagt 240
tttggaaaaa ctcttagcct accaattctt ctaagtgttt taaaatgtgg gagccagtac 300
acatgaagtt atagagtgtt ttaatgaggc ttaaatattt accgtaacta tgaaatgcta 360
cgcatatcat gctgttcagg ctccgtggcc acgcaactca tactaccggt gtcgacgcca 420
ccatgcagct gcatttaccg caggttttag ctgacgctgt ctcacgcctg gtcctgggta 480
agtttggtga cctgaccgac aacttctcct cccctcacgc tcgcagaaaa gtgctggctg 540
gagtcgtcat gacaacaggc acagatgtta aagatgccaa ggtgataagt gtttctacag 600
gaggcaaatg tattaatggt gaatacatga gtgatcgtgg ccttgcatta aatgactgcc 660
atgcagaaat aatatctcgg agatccttgc tcagatttct ttatacacaa cttgagcttt 720
acttaaataa caaagatgat caaaaaagat ccatctttca gaaatcagag cgaggggggt 780
ttaggctgaa ggagaatgtc cagtttcatc tgtacatcag cacctctccc tgtggagatg 840
ccagaatctt ctcaccacat gagccaatcc tggaagaacc agcagataga cacccaaatc 900
gtaaagcaag aggacagcta cggaccaaaa tagagtctgg tcaggggacg attccagtgc 960
gctccaatgc gagcatccaa acgtgggacg gggtgctgca aggggagcgg ctgctcacca 1020
tgtcctgcag tgacaagatt gcacgctgga acgtggtggg catccaggga tcactgctca 1080
gcattttcgt ggagcccatt tacttctcga gcatcatcct gggcagcctt taccacgggg 1140
accacctttc cagggccatg taccagcgga tctccaacat agaggacctg ccacctctct 1200
acaccctcaa caagcctttg ctcagtggca tcagcaatgc agaagcacgg cagccaggga 1260
aggcccccaa cttcagtgtc aactggacgg taggcgactc cgctattgag gtcatcaacg 1320
ccacgactgg gaaggatgag ctgggccgcg cgtcccgcct gtgtaagcac gcgttgtact 1380
gtcgctggat gcgtgtgcac ggcaaggttc cctcccactt actacgctcc aagattacca 1440
agcccaacgt gtaccatgag tccaagctgg cggcaaagga gtaccaggcc gccaaggcgc 1500
gtctgttcac agccttcatc aaggcggggc tgggggcctg ggtggagaag cccaccgagc 1560
aggaccagtt ctcactcacg ggatcccttc aactgcctcc acttgaaaga ctgacactga 1620
acatccccgc tctggtggaa aaccagaaga agtactttgg cacctacagc gtgatggcca 1680
tgctgaacgc tcagaccgtg ctggaccaca tccagaaggt ggccgatatt gagggcgagc 1740
agaacgagaa caacgagaat ctgtggtttc accccgtgat gagccacctg tacaacgcca 1800
agaacggcta cgacaagcag cccgagaaaa ccatgttcat catcgagcgg ctgcagagct 1860
acttcccatt cctgaagatc atggccgaga accagagaga gtacagcaac ggcaagtaca 1920
agcagaaccg cgtggaagtg aacagcaacg acatcttcga ggtgctgaag cgcgccttcg 1980
gcgtgctgaa gatgtacagg gacctgacca acgcatacaa gacctacgag gaaaagctga 2040
acgacggctg cgagttcctg accagcacag agcaacctct gagcggcatg atcaacaact 2100
actacacagt ggccctgcgg aacatgaacg agagatacgg ctacaagaca gaggacctgg 2160
ccttcatcca ggacaagcgg ttcaagttcg tgaaggacgc ctacggcaag aaaaagtccc 2220
aagtgaatac cggattcttc ctgagcctgc aggactacaa cggcgacaca cagaagaagc 2280
tgcacctgag cggagtggga atcgccctgc tgatctgcct gttcctggac aagcagtaca 2340
tcaacatctt tctgagcagg ctgcccatct tctccagcta caatgcccag agcgaggaac 2400
ggcggatcat catcagatcc ttcggcatca acagcatcaa gctgcccaag gaccggattc 2460
acagcgagaa gtccaacaag agcgtggcca tggatatgct caacgaagtg aagcggtgcc 2520
ccgacgagct gttcacaaca ctgtctgccg agaagcagtc ccggttcaga atcatcagcg 2580
acgaccacaa tgaagtgctg atgaagcgga gcagcgacag attcgtgcct ctgctgctgc 2640
agtatatcga ttacggcaag ctgttcgacc acatcaggtt ccacgtgaac atgggcaagc 2700
tgagatacct gctgaaggcc gacaagacct gcatcgacgg ccagaccaga gtcagagtga 2760
tcgagcagcc cctgaacggc ttcggcagac tggaagaggc cgagacaatg cggaagcaag 2820
agaacggcac cttcggcaac agcggcatcc ggatcagaga cttcgagaac atgaagcggg 2880
acgacgccaa tcctgccaac tatccctaca tcgtggacac ctacacacac tacatcctgg 2940
aaaacaacaa ggtcgagatg tttatcaacg acaaagagga cagcgcccca ctgctgcccg 3000
tgatcgagga tgatagatac gtggtcaaga caatccccag ctgccggatg agcaccctgg 3060
aaattccagc catggccttc cacatgtttc tgttcggcag caagaaaacc gagaagctga 3120
tcgtggacgt gcacaaccgg tacaagagac tgttccaggc catgcagaaa gaagaagtga 3180
ccgccgagaa tatcgccagc ttcggaatcg ccgagagcga cctgcctcag aagatcctgg 3240

-continued

```
atctgatcag cggcaatgcc cacggcaagg atgtggacgc cttcatcaga ctgaccgtgg   3300
acgacatgct gaccgacacc gagcggagaa tcaagagatt caaggacgac cggaagtcca   3360
ttcggagcgc cgacaacaag atgggaaaga gaggcttcaa gcagatctcc acaggcaagc   3420
tggccgactt cctggccaag gacatcgtgc tgtttcagcc cagcgtgaac gatggcgaga   3480
acaagatcac cggcctgaac taccggatca tgcagagcgc cattgccgtg tacgatagcg   3540
gcgacgatta cgaggccaag cagcagttca agctgatgtt cgagaaggcc cggctgatcg   3600
gcaagggcac aacagagcct catccatttc tgtacaaggt gttcgcccgc agcatccccg   3660
ccaatgccgt cgagttctac gagcgctacc tgatcgagcg gaagttctac ctgaccggcc   3720
tgtccaacga gatcaagaaa ggcaacagag tggatgtgcc cttcatccgg cgggaccaga   3780
acaagtggaa aacacccgcc atgaagaccc tgggcagaat ctacagcgag gatctgcccg   3840
tggaactgcc cagacagatg ttcgacaatg agatcaagtc ccacctgaag tccctgccac   3900
agatggaagg catcgacttc aacaatgcca acgtgaccta tctgatcgcc gagtacatga   3960
agagagtgct ggacgacgac ttccagacct tctaccagtg gaaccgcaac taccggtaca   4020
tggacatgct taagggcgag tacgacagaa agggctccct gcagcactgc ttcaccagcg   4080
tggaagagag agaaggcctc tggaaagagc gggcctccag aacagagcgg tacagaaagc   4140
aggccagcaa caagatccgc agcaaccggc agatgagaaa cgccagcagc gaagagatcg   4200
agacaatcct ggataagcgg ctgagcaaca gccggaacga gtaccagaaa agcgagaaag   4260
tgatccggcg ctacagagtg caggatgccc tgctgtttct gctggccaaa aagaccctga   4320
ccgaactggc cgatttcgac ggcgagaggt tcaaactgaa agaaatcatg cccgacgccg   4380
agaagggaat cctgagcgag atcatgccca tgagcttcac cttcgagaaa ggcggcaaga   4440
agtacaccat caccagcgag ggcatgaagc tgaagaacta cggcgacttc tttgtgctgg   4500
ctagcgacaa gaggatcggc aacctgctgg aactcgtggg cagcgacatc gtgtccaaag   4560
aggatggatc ccttcaactg cctccacttg aaagactgac actgtaccca tacgatgttc   4620
cagattacgc ttaaaagctt gaattcgatc tttttccctc tgccaaaaat tatggggaca   4680
tcatgaagcc ccttgagcat ctgacttctg gctaataaag gaaatttatt ttcattgcaa   4740
tagtgtgttg gaattttttg tgtctctcac tcggcggccg caggaacccc tagtgatgga   4800
gttggccact ccctctctgc gcgctcgctc gctcactgag gccgggcgac caaaggtcgc   4860
ccgacgcccg ggctttgccc gggcggcctc agtgagcgag cgagcgcgca gctgcctgca   4920
gg                                                                  4922
```

<210> SEQ ID NO 8
<211> LENGTH: 4922
<212> TYPE: DNA
<213> ORGANISM: Artificial Sequence
<220> FEATURE:
<223> OTHER INFORMATION: Synthetic

<400> SEQUENCE: 8

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggcctct agaatggagg cggtactatg tagatgagaa    180
ttcaggagca aactgggaaa agcaactgct tccaaatatt tgtgattttt acagtgtagt    240
tttggaaaaa ctcttagcct accaattctt ctaagtgttt taaaatgtgg gagccagtac    300
acatgaagtt atagagtgtt ttaatgaggc ttaaatattt accgtaacta tgaaatgcta    360
```

```
cgcatatcat gctgttcagg ctccgtggcc acgcaactca tactaccggt gtcgacgcca    420
ccatgcttca actgcctcca cttgaaagac tgacactgaa catccccgct ctggtggaaa    480
accagaagaa gtactttggc acctacagcg tgatggccat gctgaacgct cagaccgtgc    540
tggaccacat ccagaaggtg gccgatattg agggcgagca gaacgagaac aacgagaatc    600
tgtggtttca ccccgtgatg agccacctgt acaacgccaa gaacggctac gacaagcagc    660
ccgagaaaac catgttcatc atcgagcggc tgcagagcta cttcccattc ctgaagatca    720
tggccgagaa ccagagagag tacagcaacg gcaagtacaa gcagaaccgc gtggaagtga    780
acagcaacga catcttcgag gtgctgaagc gcgccttcgg cgtgctgaag atgtacaggg    840
acctgaccaa cgcatacaag acctacgagg aaaagctgaa cgacggctgc gagttcctga    900
ccagcacaga gcaacctctg agcggcatga tcaacaacta ctacacagtg gccctgcgga    960
acatgaacga gagatacggc tacaagacag aggacctggc cttcatccag gacaagcggt   1020
tcaagttcgt gaaggacgcc tacggcaaga aaaagtccca agtgaatacc ggattcttcc   1080
tgagcctgca ggactacaac ggcgacacac agaagaagct gcacctgagc ggagtgggaa   1140
tcgccctgct gatctgcctg ttcctggaca agcagtacat caacatcttt ctgagcaggc   1200
tgcccatctt ctccagctac aatgcccaga gcgaggaacg gcggatcatc atcagatcct   1260
tcggcatcaa cagcatcaag ctgcccaagg accggattca cagcgagaag tccaacaaga   1320
gcgtggccat ggatatgctc aacgaagtga agcggtgccc cgacgagctg ttcacaacac   1380
tgtctgccga gaagcagtcc cggttcagaa tcatcagcga cgaccacaat gaagtgctga   1440
tgaagcggag cagcgacaga ttcgtgcctc tgctgctgca gtatatcgat tacggcaagc   1500
tgttcgacca catcaggttc cacgtgaaca tgggcaagct gagatacctg ctgaaggccg   1560
acaagacctg catcgacggc cagaccagag tcagagtgat cgagcagccc ctgaacggct   1620
tcggcagact ggaagaggcc gagacaatgc ggaagcaaga gaacggcacc ttcggcaaca   1680
gcggcatccg gatcagagac ttcgagaaca tgaagcggga cgacgccaat cctgccaact   1740
atccctacat cgtggacacc tacacacact acatcctgga aaacaacaag gtcgagatgt   1800
ttatcaacga caaagaggac agcgccccac tgctgcccgt gatcgaggat gatagatacg   1860
tggtcaagac aatccccagc tgccggatga gcaccctgga aattccagcc atggccttcc   1920
acatgtttct gttcggcagc aagaaaaccg agaagctgat cgtggacgtg cacaaccggt   1980
acaagagact gttccaggcc atgcagaaag aagaagtgac cgccgagaat atcgccagct   2040
tcggaatcgc cgagagcgac ctgcctcaga agatcctgga tctgatcagc ggcaatgccc   2100
acggcaagga tgtggacgcc ttcatcagac tgaccgtgga cgacatgctg accgacaccg   2160
agcggagaat caagagattc aaggacgacc ggaagtccat tcggagcgcc gacaacaaga   2220
tgggaaagag aggcttcaag cagatctcca caggcaagct ggccgacttc ctggccaagg   2280
acatcgtgct gtttcagccc agcgtgaacg atggcgagaa caagatcacc ggcctgaact   2340
accggatcat gcagagcgcc attgccgtgt acgatagcgg cgacgattac gaggccaagc   2400
agcagttcaa gctgatgttc gagaaggccc ggctgatcgg caagggcaca acagagcctc   2460
atccatttct gtacaaggtg ttcgcccgca gcatccccgc caatgccgtc gagttctacg   2520
agcgctacct gatcgagcgg aagttctacc tgaccggcct gtccaacgag atcaagaaag   2580
gcaacagagt ggatgtgccc ttcatccggc gggaccagaa caagtggaaa acacccgcca   2640
tgaagaccct gggcagaatc tacagcgagg atctgcccgt ggaactgccc agacagatgt   2700
```

```
tcgacaatga gatcaagtcc cacctgaagt ccctgccaca gatggaaggc atcgacttca   2760
acaatgccaa cgtgacctat ctgatcgccg agtacatgaa gagagtgctg gacgacgact   2820
tccagacctt ctaccagtgg aaccgcaact accggtacat ggacatgctt aagggcgagt   2880
acgacagaaa gggctccctg cagcactgct tcaccagcgt ggaagagaga gaaggcctct   2940
ggaaagagcg ggcctccaga acagagcggt acagaaagca ggccagcaac aagatccgca   3000
gcaaccggca gatgagaaac gccagcagcg aagagatcga gacaatcctg gataagcggc   3060
tgagcaacag ccggaacgag taccagaaaa gcgagaaagt gatccggcgc tacagagtgc   3120
aggatgccct gctgtttctg ctggccaaaa agaccctgac cgaactggcc gatttcgacg   3180
gcgagaggtt caaactgaaa gaaatcatgc ccgacgccga gaagggaatc ctgagcgaga   3240
tcatgcccat gagcttcacc ttcgagaaag gcggcaagaa gtacaccatc accagcgagg   3300
gcatgaagct gaagaactac ggcgacttct ttgtgctggc tagcgacaag aggatcggca   3360
acctgctgga actcgtgggc agcgacatcg tgtccaaaga ggatggatcc cttcaactgc   3420
ctccacttga aagactgaca ctgtacccat acgatgttcc agattacgct ggatcccagc   3480
tgcatttacc gcaggtttta gctgacgctg tctcacgcct ggtcctgggt aagtttggtg   3540
acctgaccga caacttctcc tcccctcacg ctcgcagaaa agtgctggct ggagtcgtca   3600
tgacaacagg cacagatgtt aaagatgcca aggtgataag tgtttctaca ggaggcaaat   3660
gtattaatgg tgaatacatg agtgatcgtg gccttgcatt aaatgactgc catgcagaaa   3720
taatatctcg gagatccttg ctcagatttc tttatacaca acttgagctt tacttaaata   3780
acaaagatga tcaaaaaaga tccatctttc agaaatcaga gcgagggggg tttaggctga   3840
aggagaatgt ccagtttcat ctgtacatca gcacctctcc ctgtggagat gccagaatct   3900
tctcaccaca tgagccaatc ctggaagaac cagcagatag acacccaaat cgtaaagcaa   3960
gaggacagct acggaccaaa atagagtctg gtcaggggac gattccagtg cgctccaatg   4020
cgagcatcca aacgtgggac ggggtgctgc aaggggagcg gctgctcacc atgtcctgca   4080
gtgacaagat tgcacgctgg aacgtggtgg gcatccaggg atcactgctc agcattttcg   4140
tggagcccat ttacttctcg agcatcatcc tgggcagcct ttaccacggg gaccaccttt   4200
ccagggccat gtaccagcgg atctccaaca tagaggacct gccacctctc tacaccctca   4260
acaagccttt gctcagtggc atcagcaatg cagaagcacg gcagccaggg aaggccccca   4320
acttcagtgt caactggacg gtaggcgact ccgctattga ggtcatcaac gccacgactg   4380
ggaaggatga gctgggccgc gcgtcccgcc tgtgtaagca cgcgttgtac tgtcgctgga   4440
tgcgtgtgca cggcaaggtt ccctcccact tactacgctc caagattacc aagcccaacg   4500
tgtaccatga gtccaagctg gcggcaaagg agtaccaggc cgccaaggcg cgtctgttca   4560
cagccttcat caaggcgggg ctgggggcct gggtggagaa gcccaccgag caggaccagt   4620
tctcactcac gtaaaagctt gaattcgatc tttttccctc tgccaaaaat tatggggaca   4680
tcatgaagcc ccttgagcat ctgacttctg gctaataaag gaaatttatt ttcattgcaa   4740
tagtgtgttg gaattttttg tgtctctcac tcggcggccg caggaacccc tagtgatgga   4800
gttggccact ccctctctgc gcgctcgctc gctcactgag gccgggcgac caaaggtcgc   4860
ccgacgcccg ggctttgccc gggcggcctc agtgagcgag cgagcgcgca gctgcctgca   4920
gg                                                                  4922
```

<210> SEQ ID NO 9
<211> LENGTH: 1158

<212> TYPE: DNA
<213> ORGANISM: Artificial Sequence
<220> FEATURE:
<223> OTHER INFORMATION: Synthetic

<400> SEQUENCE: 9
atgcagctgc atttaccgca ggttttagct gacgctgtct cacgcctggt cctgggtaag 60
tttggtgacc tgaccgacaa cttctcctcc cctcacgctc gcagaaaagt gctggctgga 120
gtcgtcatga caacaggcac agatgttaaa gatgccaagg tgataagtgt ttctacagga 180
ggcaaatgta ttaatggtga atacatgagt gatcgtggcc ttgcattaaa tgactgccat 240
gcagaaataa tatctcggag atccttgctc agatttcttt atacacaact tgagctttac 300
ttaaataaca aagatgatca aaaaagatcc atctttcaga aatcagagcg agggggggttt 360 aggctgaagg agaatgtcca gtttcatctg tacatcagca cctctccctg tggagatgcc 420
agaatcttct caccacatga gccaatcctg gaagaaccag cagatagaca cccaaatcgt 480
aaagcaagag gacagctacg gaccaaaata gagtctggtc aggggacgat tccagtgcgc 540
tccaatgcga gcatccaaac gtgggacggg gtgctgcaag gggagcggct gctcaccatg 600
tcctgcagtg acaagattgc acgctggaac gtggtgggca tccagggatc actgctcagc 660
attttcgtgg agcccattta cttctcgagc atcatcctgg gcagccttta ccacggggac 720
cacctttcca gggccatgta ccagcggatc tccaacatag aggacctgcc acctctctac 780
accctcaaca agcctttgct cagtggcatc agcaatgcag aagcacggca gccagggaag 840
gcccccaact tcagtgtcaa ctggacggta ggcgactccg ctattgaggt catcaacgcc 900
acgactggga aggatgagct gggccgcgcg tcccgcctgt gtaagcacgc gttgtactgt 960
cgctggatgc gtgtgcacgg caaggttccc tcccacttac tacgctccaa gattaccaag 1020
cccaacgtgt accatgagtc caagctggcg gcaaaggagt accaggccgc caaggcgcgt 1080
ctgttcacag ccttcatcaa ggcggggctg gggggcctggg tggagaagcc caccgagcag 1140
gaccagttct cactcacg 1158

<210> SEQ ID NO 10
<211> LENGTH: 2946
<212> TYPE: DNA
<213> ORGANISM: Artificial Sequence
<220> FEATURE:
<223> OTHER INFORMATION: Synthetic

<400> SEQUENCE: 10
aacatccccg ctctggtgga aaaccagaag aagtactttg gcacctacag cgtgatggcc 60
atgctgaacg ctcagaccgt gctggaccac atccagaagg tggccgatat tgagggcgag 120
cagaacgaga acaacgagaa tctgtggttt caccccgtga tgagccacct gtacaacgcc 180
aagaacggct acgacaagca gcccgagaaa accatgttca tcatcgagcg gctgcagagc 240
tacttcccat tcctgaagat catggccgag aaccagagag agtacagcaa cggcaagtac 300
aagcagaacc gcgtggaagt gaacagcaac gacatcttcg aggtgctgaa gcgcgccttc 360
ggcgtgctga agatgtacag ggacctgacc aacgcataca agacctacga ggaaaagctg 420
aacgacggct gcgagttcct gaccagcaca gagcaacctc tgagcggcat gatcaacaac 480
tactacacag tggccctgcg gaacatgaac gagagatacg gctacaagac agaggacctg 540
gccttcatcc aggacaagcg gttcaagttc gtgaaggacg cctacggcaa gaaaaagtcc 600
caagtgaata ccggattctt cctgagcctg caggactaca acggcgacac acagaagaag 660

-continued ctgcacctga gcggagtggg aatcgccctg ctgatctgcc tgttcctgga caagcagtac 720
atcaacatct ttctgagcag gctgcccatc ttctccagct acaatgccca gagcgaggaa 780
cggcggatca tcatcagatc cttcggcatc aacagcatca agctgcccaa ggaccggatt 840
cacagcgaga agtccaacaa gagcgtggcc atggatatgc tcaacgaagt gaagcggtgc 900
cccgacgagc tgttcacaac actgtctgcc gagaagcagt cccggttcag aatcatcagc 960
gacgaccaca atgaagtgct gatgaagcgg agcagcgaca gattcgtgcc tctgctgctg 1020
cagtatatcg attacggcaa gctgttcgac cacatcaggt tccacgtgaa catgggcaag 1080
ctgagatacc tgctgaaggc cgacaagacc tgcatcgacg gccagaccag agtcagagtg 1140
atcgagcagc ccctgaacgg cttcggcaga ctggaagagg ccgagacaat gcggaagcaa 1200
gagaacggca ccttcggcaa cagcggcatc cggatcagag acttcgagaa catgaagcgg 1260
gacgacgcca atcctgccaa ctatccctac atcgtggaca cctacacaca ctacatcctg 1320
gaaaacaaca aggtcgagat gtttatcaac gacaaagagg acagcgcccc actgctgccc 1380
gtgatcgagg atgatagata cgtggtcaag acaatcccca gctgccggat gagcaccctg 1440
gaaattccag ccatggcctt ccacatgttt ctgttcggca gcaagaaaac cgagaagctg 1500
atcgtggacg tgcacaaccg gtacaagaga ctgttccagg ccatgcagaa agaagaagtg 1560
accgccgaga atatcgccag cttcggaatc gccgagagcg acctgcctca gaagatcctg 1620
gatctgatca gcggcaatgc ccacggcaag gatgtggacg ccttcatcag actgaccgtg 1680
gacgacatgc tgaccgacac cgagcggaga atcaagagat tcaaggacga ccggaagtcc 1740
attcggagcg ccgacaacaa gatgggaaag agaggcttca agcagatctc cacaggcaag 1800
ctggccgact tcctggccaa ggacatcgtg ctgtttcagc ccagcgtgaa cgatggcgag 1860
aacaagatca ccggcctgaa ctaccggatc atgcagagcg ccattgccgt gtacgatagc 1920
ggcgacgatt acgaggccaa gcagcagttc aagctgatgt tcgagaaggc ccggctgatc 1980
ggcaagggca caacagagcc tcatccattt ctgtacaagg tgttcgcccg cagcatcccc 2040
gccaatgccg tcgagttcta cgagcgctac ctgatcgagc ggaagttcta cctgaccggc 2100
ctgtccaacg agatcaagaa aggcaacaga gtggatgtgc ccttcatccg gcgggaccag 2160
aacaagtgga aaacacccgc catgaagacc ctgggcagaa tctacagcga ggatctgccc 2220
gtggaactgc ccagacagat gttcgacaat gagatcaagt cccacctgaa gtccctgcca 2280
cagatggaag gcatcgactt caacaatgcc aacgtgacct atctgatcgc cgagtacatg 2340
aagagagtgc tggacgacga cttccagacc ttctaccagt ggaaccgcaa ctaccggtac 2400
atggacatgc ttaagggcga gtacgacaga aagggctccc tgcagcactg cttcaccagc 2460
gtggaagaga gagaaggcct ctggaaagag cgggcctcca gaacagagcg gtacagaaag 2520
caggccagca acaagatccg cagcaaccgg cagatgagaa acgccagcag cgaagagatc 2580
gagacaatcc tggataagcg gctgagcaac agccggaacg agtaccagaa aagcgagaaa 2640
gtgatccggc gctacagagt gcaggatgcc ctgctgtttc tgctggccaa aaagaccctg 2700
accgaactgg ccgatttcga cggcgagagg ttcaaactga aagaaatcat gcccgacgcc 2760
gagaagggaa tcctgagcga gatcatgccc atgagcttca ccttcgagaa aggcggcaag 2820
aagtacacca tcaccagcga gggcatgaag ctgaagaact acggcgactt ctttgtgctg 2880
gctagcgaca agaggatcgg caacctgctg gaactcgtgg gcagcgacat cgtgtccaaa 2940
gaggat 2946

<210> SEQ ID NO 11
<211> LENGTH: 63
<212> TYPE: RNA
<213> ORGANISM: Artificial Sequence
<220> FEATURE:
<223> OTHER INFORMATION: Synthetic polynucleotide

<400> SEQUENCE: 11
guaauugaau gcagaguaga ggccgcagga uaguuuagaa cauucuaugg aaagagauuc 60
cag 63

<210> SEQ ID NO 12
<211> LENGTH: 45
<212> TYPE: RNA
<213> ORGANISM: Artificial Sequence
<220> FEATURE:
<223> OTHER INFORMATION: Synthetic polynucleotide

<400> SEQUENCE: 12
cuuuccauag aauguucuaa accauccugc ggccucuacu cugca 45

<210> SEQ ID NO 13
<211> LENGTH: 99
<212> TYPE: DNA
<213> ORGANISM: Artificial Sequence
<220> FEATURE:
<223> OTHER INFORMATION: Synthetic polynucleotide

<400> SEQUENCE: 13
gtactcacag tcatggggct catggccctg ttggatggag aacaactctg ggcagaggtc 60
tcaaaggctg gggctgtgtt ggacagcaat catacagtg 99

<210> SEQ ID NO 14
<211> LENGTH: 33
<212> TYPE: PRT
<213> ORGANISM: Artificial Sequence
<220> FEATURE:
<223> OTHER INFORMATION: Synthetic polypeptide

<400> SEQUENCE: 14

Val Leu Thr Val Met Gly Leu Met Ala Leu Leu Asp Gly Glu Gln Leu
1 5 10 15

Trp Ala Glu Val Ser Lys Ala Gly Ala Val Leu Asp Ser Asn His Thr
20 25 30

Val

<210> SEQ ID NO 15
<211> LENGTH: 99
<212> TYPE: DNA
<213> ORGANISM: Artificial Sequence
<220> FEATURE:
<223> OTHER INFORMATION: Synthetic polynucleotide

<400> SEQUENCE: 15
gtactcacag tcatggggct catggccctg ttggatggag aacaactcta ggcagaggtc 60
tcaaaggctg gggctgtgtt ggacagcaat catacagtg 99

<210> SEQ ID NO 16
<211> LENGTH: 16
<212> TYPE: PRT
<213> ORGANISM: Artificial Sequence
<220> FEATURE:
<223> OTHER INFORMATION: Synthetic polypeptide -continued

```
<400> SEQUENCE: 16

Val Leu Thr Val Met Gly Leu Met Ala Leu Leu Asp Gly Glu Gln Leu
1               5                   10                  15


<210> SEQ ID NO 17
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 17

Ala Glu Val Ser Lys Ala Gly Ala Val Leu Asp Ser Asn His Thr Val
1               5                   10                  15
```